(12) United States Patent
Roe et al.

(10) Patent No.: US 9,167,992 B2
(45) Date of Patent: Oct. 27, 2015

(54) LANCET DRIVE SYSTEM DEPTH CONTROL METHOD AND TEST STRIP LOCATION METHODS

(75) Inventors: Steven N. Roe, San Mateo, CA (US); Michael Keil, Ludwigshafen (DE); Charles C. Raney, Camdenton, MO (US)

(73) Assignee: Roche Diabetes Care, Inc., Indianapolis, IN (US)

(*) Notice: Subject to any disclaimer, the term of this patent is extended or adjusted under 35 U.S.C. 154(b) by 461 days.

(21) Appl. No.: 12/938,858

(22) Filed: Nov. 3, 2010

(65) Prior Publication Data

US 2012/0109176 A1     May 3, 2012

(51) Int. Cl.
| | |
|---|---|
| *A61B 5/00* | (2006.01) |
| *A61B 17/14* | (2006.01) |
| *A61B 17/32* | (2006.01) |
| *A61B 5/15* | (2006.01) |
| *A61B 5/151* | (2006.01) |

(52) U.S. Cl.
CPC ............ *A61B 5/1411* (2013.01); *A61B 5/15019* (2013.01); *A61B 5/150022* (2013.01); *A61B 5/15113* (2013.01); *A61B 5/15117* (2013.01); *A61B 5/15128* (2013.01); *A61B 5/15186* (2013.01); *A61B 5/150412* (2013.01); *A61B 5/1513* (2013.01); *A61B 5/1519* (2013.01); *A61B 5/15115* (2013.01); *A61B 5/15126* (2013.01); *A61B 5/15194* (2013.01); *A61B 5/150198* (2013.01)

(58) Field of Classification Search
CPC ............. A61B 5/1411; A61B 5/15186; A61B 5/15115; A61B 5/15126; A61B 5/15128; A61B 5/15019; A61B 5/150198

USPC .................................... 600/583; 606/181, 182
See application file for complete search history.

(56) References Cited

U.S. PATENT DOCUMENTS

| | | | |
|---|---|---|---|
| 4,924,879 A | 5/1990 | O'Brien | |
| 6,409,740 B1 * | 6/2002 | Kuhr et al. | ..................... 606/182 |
| 6,602,268 B2 | 8/2003 | Kuhr et al. | |

(Continued)

FOREIGN PATENT DOCUMENTS

| | | |
|---|---|---|
| EP | 2 221 000 A1 | 8/2010 |
| WO | 2006092309 A2 | 9/2006 |

(Continued)

OTHER PUBLICATIONS

International PatentApplication No. PCT/EP2011/005471 International Search Report and Written Opinion mailed Feb. 2, 2012.

*Primary Examiner* — Devin Henson
(74) *Attorney, Agent, or Firm* — Woodard, Emhardt, Moriarty, McNett & Henry LLP

(57) ABSTRACT

Adjustment mechanisms are used in conjunction with integrated lancet test strips to adjust the position of the drive system, engagement system, or the drive coupling in a fixed stroke lancing system to thereby adjust the penetration depth of the lancet. In a variable drive stroke lancing system, the lancet penetration depth is adjusted by changing the stroke length of a drive system. The stroke length of a drive system is adjusted by rotating a cam or sliding a cam in a cam type drive system. In either the fixed or the variable drive stroke lancing system, the test strip and/or guidance foil of the integrated lancet test strip is immobilized while the lancet is actuated.

16 Claims, 20 Drawing Sheets

(56) References Cited

U.S. PATENT DOCUMENTS

| | | | |
|---|---|---|---|
| 6,749,618 B2* | 6/2004 | Levaughn et al. | 606/182 |
| 6,858,015 B2* | 2/2005 | List | 600/583 |
| 2004/0092996 A1 | 5/2004 | List et al. | |
| 2004/0267300 A1 | 12/2004 | Mace | |
| 2005/0154410 A1 | 7/2005 | Conway et al. | |
| 2005/0234494 A1* | 10/2005 | Conway et al. | 606/181 |
| 2005/0245845 A1 | 11/2005 | Roe et al. | |
| 2006/0155317 A1 | 7/2006 | List | |
| 2006/0241517 A1* | 10/2006 | Fowler et al. | 600/583 |
| 2007/0100256 A1 | 5/2007 | Sansom | |
| 2007/0167869 A1* | 7/2007 | Roe | 600/583 |
| 2008/0007141 A1 | 1/2008 | Deck | |
| 2008/0082023 A1* | 4/2008 | Deck et al. | 600/583 |
| 2008/0082117 A1 | 4/2008 | Ruf | |
| 2008/0146966 A1 | 6/2008 | Levaughn et al. | |
| 2010/0021342 A1 | 1/2010 | Joseph et al. | |
| 2010/0042129 A1* | 2/2010 | Curry | 606/181 |
| 2010/0168618 A1 | 7/2010 | List | |

FOREIGN PATENT DOCUMENTS

| | | |
|---|---|---|
| WO | WO 2007/130830 A2 | 11/2007 |
| WO | WO 2010/080585 A1 | 7/2010 |

* cited by examiner

LANCET DRIVE SYSTEM DEPTH CONTROL METHOD AND TEST STRIP LOCATION METHODS

BACKGROUND

The present invention generally concerns techniques and mechanisms to adjust the range of motion of a piercing member in a lancet integrated test strip. The present invention also concerns techniques and mechanisms that engage and drive the lancet as well as immobilize a test strip during the skin piercing process to ensure independent movement of the piercing member relative to the test strip.

Decreasing the amount of pain associated with forming an incision for bodily fluid testing is typically very desirable for users. One technique employed for decreasing pain includes adjusting the penetration depth of a bare lancet. Typically an adjustable cap is attached to the exterior of an incision forming end of a lancet driver housing the bare lancet. The cap is adjusted to limit the penetration depth of the lancet; however, the lancet moves the same distance to form an incision no matter how the cap is adjusted. In other words, the stroke length of the bare lancet remains fixed while the relative end position of the cap is adjusted to adjust the penetration depth of the lancet. A user of these lancet drivers also requires additional equipment to store a test strip and display test results. All of this separate equipment is more burdensome for users. Therefore, many users or patients requiring bodily fluid testing or blood glucose testing might prefer to use lancet integrated test strips ("LITs") to lance, collect, and test a bodily fluid sample. Also the lancet is assured to be sharp and sterile for each use compared to traditional lancet which dull with use and progressively cause more pain. Additionally, LIT eliminates lancet cross contamination as the lancet is thrown away with the test strip, making it ideal for hospital use where cross contamination is a real concern.

Thus, there is a need for improvement in this field.

SUMMARY

The inventors have found that it is desirable to attach an adjustment mechanism onto a portion of a meter in which the adjustment mechanism changes the starting position of various parts of a drive system within the meter such that the displacement of a lancet of an LIT is adjusted prior to actuation of the piercing member. In one form, an adjustment mechanism is attached to a drive actuator to adjust the starting position of a driver. In another embodiment, an adjustment mechanism is positioned on an engagement housing to adjust the starting position of the lancet engagement blade relative to the test strip. In yet another embodiment, an adjustment mechanism is positioned on a drive shaft to vary the starting position of a drive coupling member. All of these embodiments accomplish the task of changing the extended position or depth of the LIT lancet into the skin of the user. These inventions are needed as it is not possible to use an adjustment cap with an LIT as it is traditionally done with standard bare lancets. This is because an LIT is open or uncovered to apply the blood sample to the test strip end after the pricking event is accomplished. If a cap was positioned on a LIT, then the cap would cover the test strip end and the cap would need to be removed by the user which would be very difficult and inconvenient while expressing blood and handling the application to the end of the test strip.

In another embodiment, the inventors have also found that it is desirable to adjust a stroke length of a variable drive stroke lancing system to adjust the range of motion of the lancet of an LIT during actuation. With this adjustment system, the stroke of the drive actuator is adjusted which correspondingly adjusts the movement of the lancet. Beneficially it has been found that one embodiment of the variable stroke drive system causes the lancet to move in a simple harmonic motion upon actuation. As such, the lancet does not abruptly stop when the lancet is fully actuated as compared to a ballistic type driver that causes the lancet to come to an abrupt stop when the lancet reaches full penetration in skin. The abrupt stop of the lancet causes additional pain for the user as compared to the simple harmonic motion of the lancet driven by the variable stroke drive system. Another benefit of the simple harmonic motion of the lancet upon actuation by the variable drive stroke lancing system is a low amount of transfer vibration to the user which results in reduced pain for the user as compared to a ballistic type driver which has a higher amount of transfer vibration.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
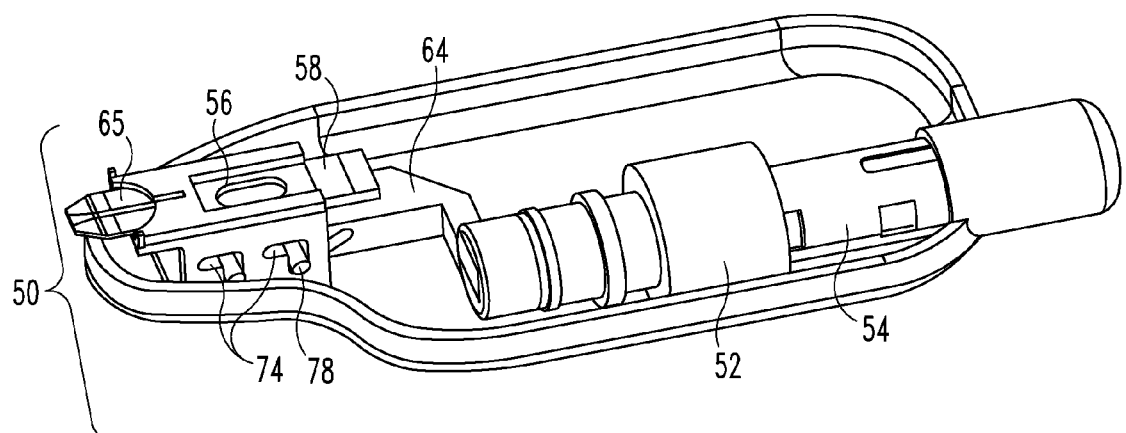
FIG. 1 is a cut-away top perspective view of a dual cam engagement system according to one embodiment.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

The present application generally concerns systems and techniques for adjusting or limiting the range of motion of piercing members, such as lancets. By decreasing the range of motion of a lancet, the penetration depth into skin by the lancet is adjusted. These penetration depth adjustment systems are used in conjunction with lancet integrated test strips (LITs). A dual cam engagement system having a fixed stroke length is configured to drive the lancet into the skin. Various types of adjustment mechanisms can be positioned on a particular component of this fixed stroke lancet drive system to adjust a starting position of the drive system and therefore the end position or depth into the skin by the lancet. The fixed stroke lancet drive system includes a cam engagement housing that holds an integrated lancet test strip, a cam engagement member, and a driver to move the lancet to form an incision in skin. The cam engagement housing or test strip holder maintains the test strip in a fixed position and allows for independent movement of the lancet to a desired penetration depth by an engagement blade and drive mechanism. The cam engagement member is operatively disposed between the driver and a drive actuator in order to transmit the firing force from the drive actuator to the lancet. The drive actuator includes a firing mechanism that moves the cam engagement member. In one embodiment, an adjustment mechanism is positioned on the drive actuator to adjust the starting position of the drive mechanism. In another embodiment, an adjustment mechanism is positioned on the cam engagement housing to adjust the cam engagement housing and the corresponding position of a cam engagement member relative to the test strip. The firing mechanism further includes a drive shaft upon which yet another type of adjustment mechanism can be positioned to vary the starting position of the cam engagement member in a third embodiment.

In the fixed stroke lancet drive system, the stroke length of the drive system that fires the lancet remains constant, and the distance that the lancet is extended can be adjusted by changing the relative position of: (1) the drive system, (2) the engagement system/test strip holder, and/or (3) the cam engagement member. In each case, an adjustment mechanism moves the particular component forward or backward in a continuous or incremental fashion. In some embodiments the particular component is moved in 0.15 mm increments and the particular component is moved a total distance from approximately 0.8 mm to about 2.3 mm.

An example of a drive system or dual cam engagement system 50 is illustrated in FIGS. 1, 2, 3, 4a, 4b, 5, and 6 and described herein. A brief overview of the drive system 50 is described next. The drive system 50 includes an adjustment mechanism 52 that is positioned on a drive actuator 54 of the drive system 50 to adjust a starting position of the drive actuator 54. The drive system 50 includes a cam engagement housing 56 that holds an integrated lancet test strip 58 that comprises a test strip 65 and receives a driver 60 and a cam engagement member 64. Integrated lancet test strip 58 is similar to the integrated lancet test strip described in application Ser. No. 11/070,502, filed Mar. 2, 2005, which is hereby incorporated by reference. Therefore, for the sake of brevity similar features for the integrated lancet test strip will not be described. The integrated lancet test strip 58 has a lancet 62, a guidance foil 63, and a test strip (not illustrated in FIG. 4b). The driver 60 engages and moves the lancet 62 while the guidance foil 63 remains stationary in the cam engagement housing 56. The drive system 50 also includes a cam engagement member 64 that is configured to connect the drive actuator 54 with the driver 60. The drive actuator 54 includes a firing mechanism (not illustrated) that engages and moves the cam engagement member 64.

Figure 6:
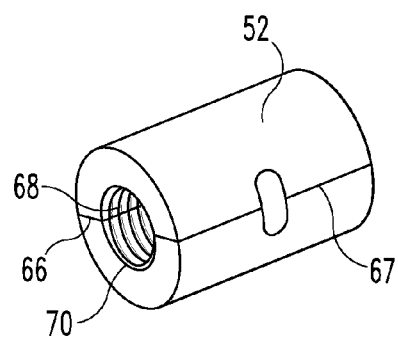
FIG. 6 is a perspective view of a second embodiment of an adjustment mechanism of the dual cam engagement system in FIG. 1.

In one form, adjustment mechanism 52, illustrated in FIG. 6, is a tubular shape that is configured to attach to the drive actuator 54. In the illustrated embodiment, adjustment mechanism 52 is formed by two parts with a hinge 66 about which the parts of adjustment mechanism 52 open to allow the adjustment mechanism 52 to attach onto the drive actuator 54. The adjustment mechanism 52 includes a clasp 67 or other closure mechanism which locks both parts of the adjustment mechanism 52 together when in a closed position. In another embodiment, the adjustment mechanism 52 is formed by two parts that snap together. The adjustment mechanism 52 defines a hollow interior bore 68 having a plurality of threads 70. The interior bore 68 and plurality of threads 70 are configured to threadedly attach to drive actuator 54 and the firing mechanism. Rotation of the adjustment mechanism 52 about the drive actuator 54 moves the firing mechanism either forward or backward by an incremental amount to adjust the start position of the firing mechanism and by connection also moving the cam engagement member 64 as described below. By adjusting the start position of the firing mechanism, the distance the lancet 62 moves is also adjusted. In other words, the depth of penetration of the lancet 62 is controlled by moving the firing mechanism either towards a direction of lancing or away from a direction of lancing. The movement of the firing mechanism controls the amount of the stroke applied to moving the lancet forward as distance on drive coupling member slots 82 is either added or subtracted to the distance pins 78 must move along drive coupling member slots 82, as described below.

Figure 4A:
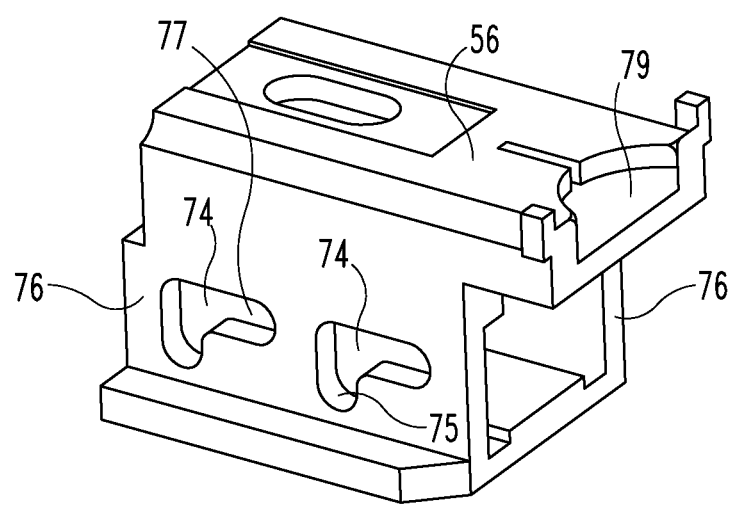
FIG. 4a is a top perspective view of a cam engagement housing of the dual cam engagement system in FIG. 1.
Figure 4B:
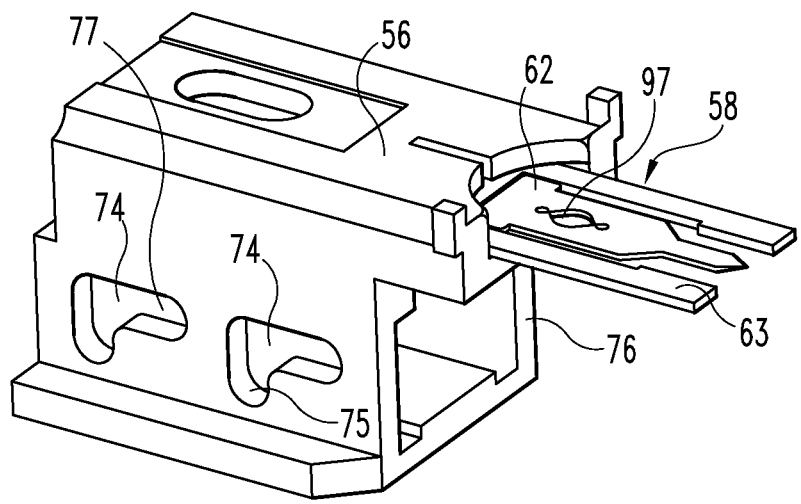
FIG. 4b is a top perspective view of the cam engagement housing of FIG. 4a including a lancet and guidance foil of an integrated lancing test strip.

The cam engagement housing 56 illustrated in FIGS. 4a and 4b, is configured to hold the integrated lancet test strip 58, the driver 60, and the cam engagement member 64. The cam engagement housing 56 includes a pair of sidewalls 76. Each of the pair of sidewalls 76 defines a pair of engagement slots 74. Each of the pair of engagement slots 74 is configured to receive a pin 78 on the driver 60. In the illustrated embodiment, each of the pair of engagement slots 74 has a substantially vertical portion 75 that intersects with a substantially horizontal portion 77. The cam engagement housing 56 also defines a channel 79 sized to retain the integrated lancet test strip 58 and restrain guidance foil 63 from movement.

Figure 2:
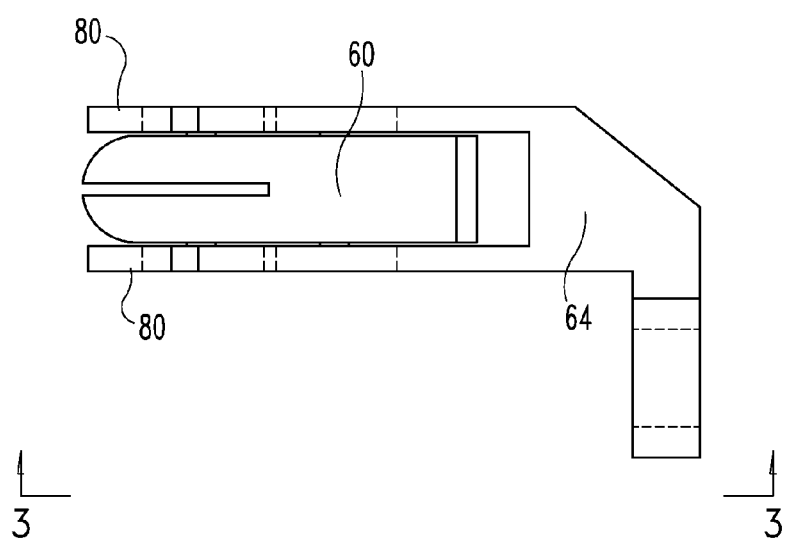
FIG. 2 is a top view of a first cam engagement member and a driver of the dual cam engagement system in FIG. 1.
Figure 3:
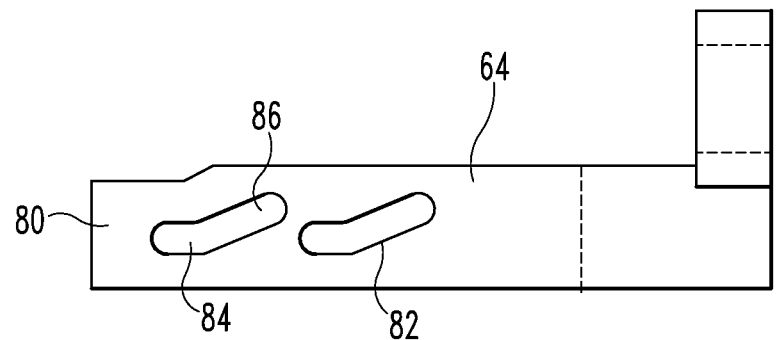
FIG. 3 is a side view of the first cam engagement member in FIG. 2.

One embodiment, illustrated in FIGS. 2 and 3, shows the cam engagement member 64 having a pair of arms 80 sized and positioned to receive the driver 60. The pair of arms 80 is separated by a distance corresponding to the width of the driver 60. The length of the pair of arms 80 is about the same length as the driver 60. At least one of the pair of arms 80 defines a pair of drive coupling member slots 82. In this form, each of the pair of drive coupling member slots 82 has a substantially horizontal portion 84 that extends to an angled portion 86. When the driver 60 is assembled with the cam engagement member 64, a pin 78 on the driver 60 extends through one of the drive coupling member slots 82 and rides along the drive coupling member slot 82 when the driver 60 is actuated as described in more detail below.

Figure 5:
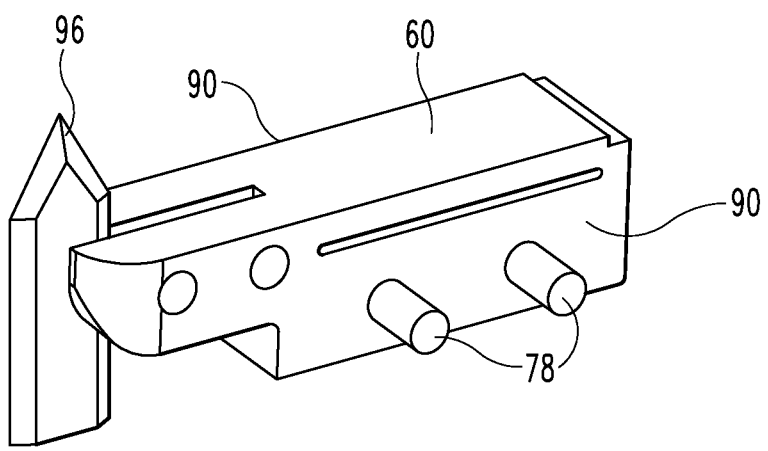
FIG. 5 is a top perspective view of a blade and a driver of the dual cam engagement system in FIG. 1.

The driver 60 is illustrated in one form in FIG. 5. As mentioned previously, the driver 60 includes a pair of pins 78 on two sides 90. One pair of the pins 78 is positioned on one of the sides 90 such that a single pin 78 fits through a single drive coupling member slot 82 and a single engagement slot 74.

When the cam engagement member 64, driver 60, and cam engagement housing 56 are assembled together, each of the pins 78 extend from the driver 60 through one of the drive coupling member slots 82 on the cam engagement member 64 and through one of the engagement slots 74 on the cam engagement housing 56. In the initial, pre-actuation position, the pin 78 rests in horizontal portion 84 of the cam engagement member 64 and the vertical portion 75 of the cam engagement housing 56. Upon actuation of the cam engagement member 64, the pin 78 travels along the horizontal portion 84 of the cam engagement member 64 until the pin 78 reaches the angled portion 86. As the cam engagement member 64 continues to move toward the lancet 62, the pin 78 travels along the angled portion 86 and the pin 78 also travels along or up the vertical portion 75 of the cam engagement housing 56. As the pin 78 travels along the vertical portion 75, the driver 60 is also lifted up towards the lancet 62 such that a lancet engagement blade 96 on the driver 60 enters an engagement notch 97 in the lancet 62. Once the pin 78 reaches the top of the vertical portion 75 and the end of the angled portion 86, the pin 78 travels along horizontal portion 77 to a fully actuated incision forming position. As the pin 78 travels along horizontal portion 77, the driver 60 moves the lancet 62 to cause the lancet 62 to extend from the guidance foil 63 for forming an incision. After the lancet 62 forms the incision, the movement of the cam engagement member 64 and the driver 60 are reversed to move the lancet 62 back into the guidance foil 63 for safe disposal of the integrated lancet test strip 58.

To form a deep incision in tissue with the lancet 62, the firing mechanism is moved toward a direction of lancing by rotation of adjustment mechanism 52. As such, pins 78 on driver 60 travel in a forward or lancing direction along a horizontal portion 84 of drive coupling member slots 82 prior to actuation of lancet 62. To form a shallow incision in tissue, the firing mechanism is moved rearwardly or away from a direction of lancing by rotation of adjustment mechanism 52. As such, pins 78 on driver 60 travel in a rearward direction along horizontal portion 84 of drive coupling member slots 82 prior to actuation of lancet 62.

Figure 7:
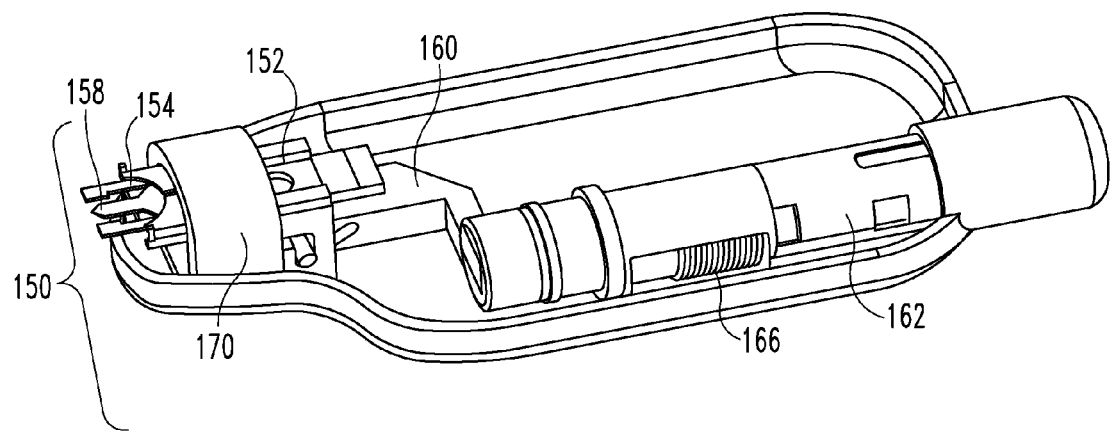
FIG. 7 is a cut-away top perspective view of a dual cam engagement system according to a third embodiment.
Figure 8:
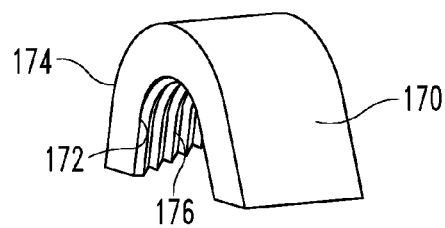
FIG. 8 is a perspective view of an adjustment mechanism of the dual cam engagement system in FIG. 7.
Figure 9:
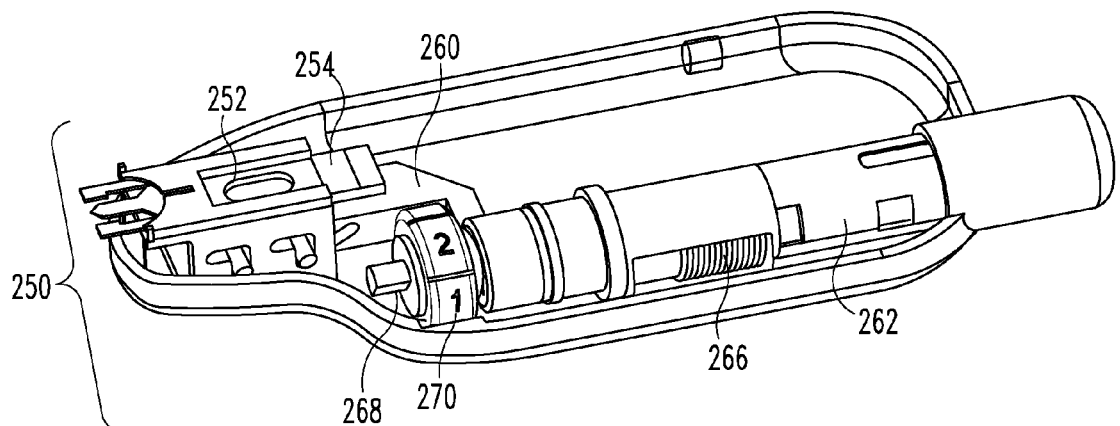
FIG. 9 is a cut-away top perspective view of a dual cam engagement system according to a third embodiment.
Figure 10:
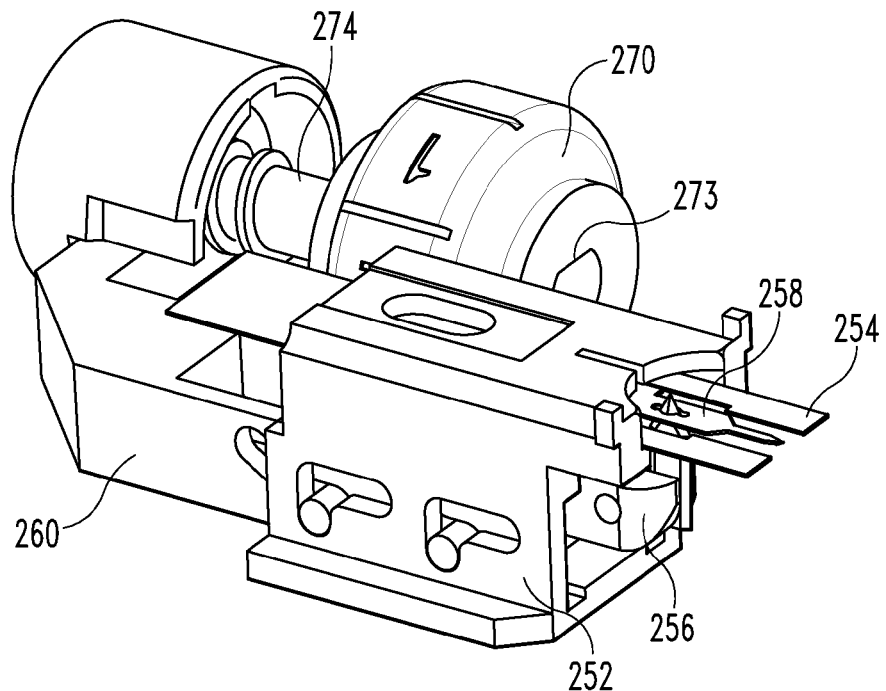
FIG. 10 is a perspective view of an adjustment mechanism of the dual cam engagement system in FIG. 9 with the lancet of an integrated lancing test strip fully retracted.
Figure 11:
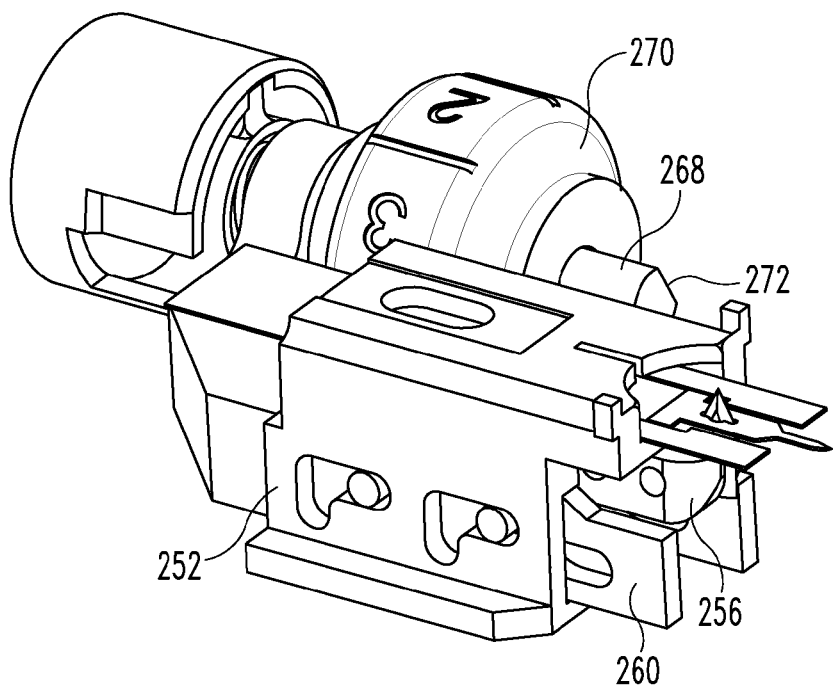
FIG. 11 is a perspective view of an adjustment mechanism of the dual cam engagement system in FIG. 9 with the lancet of an integrated lancet test strip in a fully actuated incision forming position.

In another embodiment, a drive or dual cam engagement system 150 is illustrated in FIGS. 7 and 8 and described herein. The drive system 150 is similar to drive system 50; therefore, for the sake of brevity similar features will not be described. Drive system 150 and drive system 50 both adjust or limit the movement of the lancet to adjust the penetration depth of the lancet while the test strip and guidance foil remain in a fixed position. However, drive system 150 includes an adjustment mechanism 170 that is positioned on a cam engagement housing 152 of the drive system 150 to adjust a starting position of the cam engagement housing 152.

The cam engagement housing 152 holds an integrated lancet test strip 154, a cam engagement member 160, and a driver that engages and moves a lancet 158 of the integrated lancet test strip 154. The cam engagement member 160 is configured to connect a drive actuator 162 with the driver. The drive actuator 162 includes a firing mechanism 166 that engages and moves the cam engagement member 160. The cam engagement housing 152 includes a plurality of threads on an exterior surface of the cam engagement housing 152.

In the illustrated form, adjustment mechanism 170 as shown in FIG. 8 is a semi-circular or arch shape that is configured to attach to the cam engagement housing 152. In this form, the adjustment mechanism 170 has an interior surface 172 and an exterior surface 174. The interior surface 172 includes a plurality of threads 176 that are configured to threadedly attach to a plurality of threads on the cam engagement housing 152. Tuning of the adjustment mechanism 170 to the cam engagement housing 152 moves the cam engagement housing 152 either forward or backward by an incremental amount to adjust the start position of the cam engagement member 160. By adjusting the start position of the cam engagement member 160, the distance the lancet penetrates into tissues varies. The depth of penetration of the lancet is controlled by moving the cam engagement member 160 either towards a direction of lancing or away from a direction of lancing. To form a deep incision in tissue, the cam engagement housing 152 is moved toward a direction of lancing or forwardly. To form a shallow incision in tissue, the cam engagement housing 152 is moved rearwardly or away from a direction of lancing.

In a third embodiment, a drive or dual cam engagement system 250 is illustrated in FIGS. 9, 10, 11, and 12. The drive system 250 is similar to drive system 50; therefore, for the sake of brevity similar features will not be described. Drive system 250 and drive system 50 both adjust or limit the movement of the lancet to adjust the penetration depth of the lancet while the test strip and guidance foil remain in a fixed position. However, drive system 250 includes an adjustment mechanism 270 positioned on a drive shaft 268 to adjust a starting position of a cam engagement member 260. As described above, drive system 50 includes adjustment mechanism 52 attached to the drive actuator 54 to adjust the starting position of the firing mechanism.

The drive system 250 includes a cam engagement housing 252 that holds an integrated lancet test strip 254, a cam engagement member 260, and a driver 256 that engages and moves a lancet 258 of the integrated lancet test strip 254. The cam engagement member 260 is configured to connect a drive actuator 262 with the driver 256. The drive actuator 262 includes a firing mechanism 266 that engages and moves the cam engagement member 260. The firing mechanism 266 includes a drive shaft 268. The drive system 250 includes an adjustment mechanism 270 that is positioned on the drive shaft 268. The drive shaft 268 includes a flat portion 272 on an exterior surface 274 that contacts a similarly sized flat portion 273 on an interior surface 271 of adjustment mechanism 270 to lock the adjustment mechanism 270 to the drive shaft 268.

Figure 12:
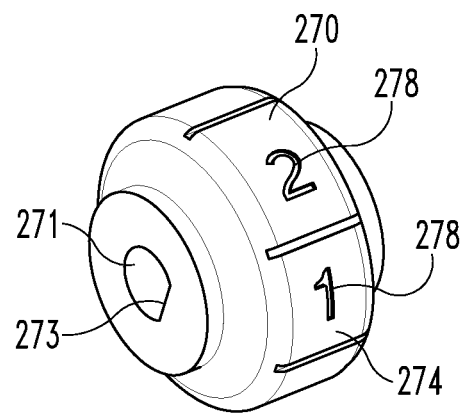
FIG. 12 is a perspective view of a depth adjustment wheel mechanism of the dual cam engagement system in FIG. 9.
Figure 13:
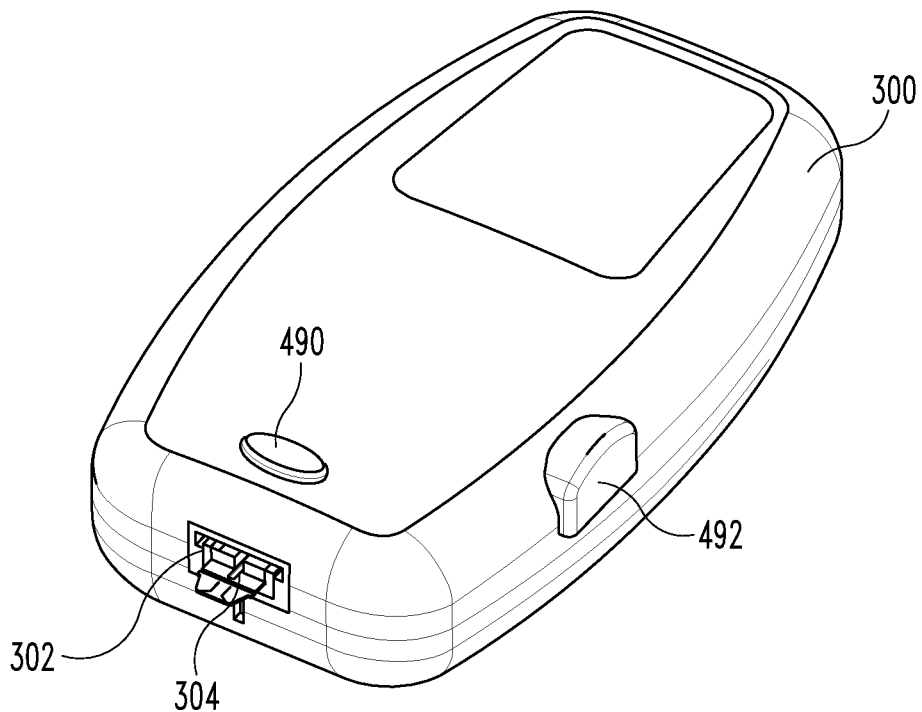
FIG. 13 is a top perspective view of a meter according to a further embodiment that includes a variable stroke drive.
Figure 14:
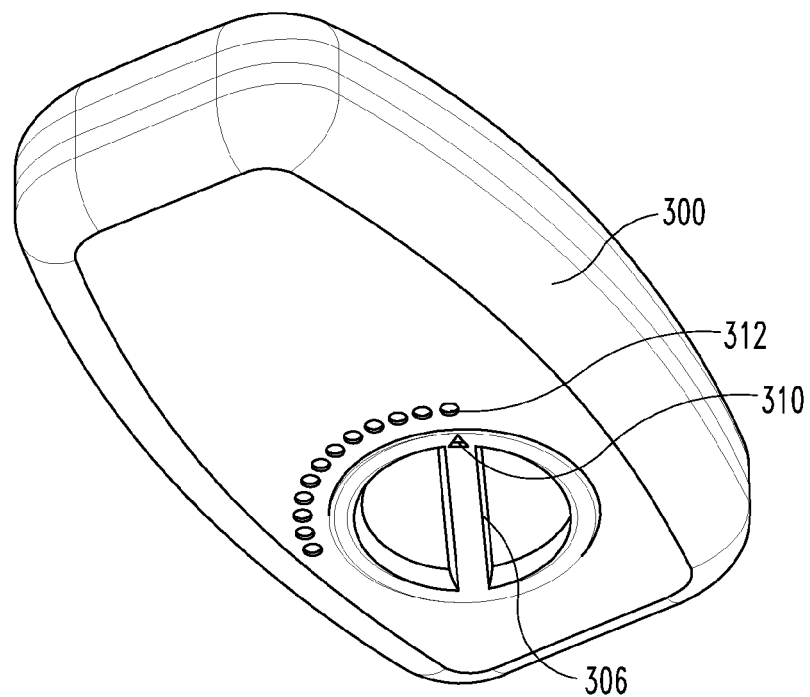
FIG. 14 is a bottom perspective view of the meter in FIG. 13.

Beneficially adjustment mechanism 270 illustrated in FIG. 12 is very small compared to the size of the drive system 250 therefore packaging for the drive system 250 does not need to be changed or reconfigured for inclusion of the adjustment mechanism 270. Adjustment mechanism 270 has a ring shape with an interior surface 271 and an exterior surface 274. The interior surface 271 includes a flat portion 273 that is configured to rest against flat portion 272 on the drive shaft 268 such that rotation of the adjustment mechanism 270 causes rotation of the drive shaft 268. Rotation of the drive shaft 268 moves the cam engagement member 260 either forward or backward by an incremental amount to adjust the start position of the cam engagement member 260. In one form, adjustment mechanism 270 includes a plurality of numbers or markers 278 that aid a user in adjusting the rotation of the adjustment mechanism 270. By adjusting the start position of the cam engagement member 260, the distance the lancet moves and penetrates into a tissue can vary while the test strip and guidance foil remain stationary. The depth of penetration of the lancet and movement of the lancet are controlled by moving the cam engagement member 260 either towards a direction of lancing or away from a direction of lancing.

In a variable drive stroke lancing system, the lancet penetration depth can be adjusted by controlling the stroke length of the drive system. The drive system in one particular arrangement includes a cam type drive system in which the rotary motion of a cam is converted to a linear motion of a cam follower that in turn fires the lancet. For the cam type system, the stroke length is a function of the eccentricity of the cam. The eccentricity may be adjusted by rotation or sliding of the drive cam relative to its pivot or point of rotation point. In another form, an inner wheel (drive cam) is eccentrically mounted to an outer wheel, which functions as a dial. When a user pushes on the outer wheel, it will engage the inner wheel and allow the user to adjust the eccentricity of the drive wheel.

One type of a meter 300 defining an integrated lancet test strip opening 302 for an integrated lancet test strip 304 is illustrated in FIGS. 13, 14, 15, 16, 17, 18, 19, 20, 21, 22, and 23. Illustrated in FIG. 14, a bottom side of meter 300 includes a knob 306 for adjusting the stroke length of a drive system 308. Knob 306 includes a designator 310. The bottom side of meter 300 includes a plurality of markers 312 that align with designator 310 as the knob 306 is rotated. A top side of meter 300 includes a button 490 that connects with a top platform 412 to aid in insertion of the integrated lancet test strip 304 into meter 300, as described in more detail below. A side of meter 300 has a side button 492 that connects with a track 320, described in more detail below, such that depression of side button 492 causes a lancing, sampling, and testing event with the integrated lancet test strip 304.

Figure 15:
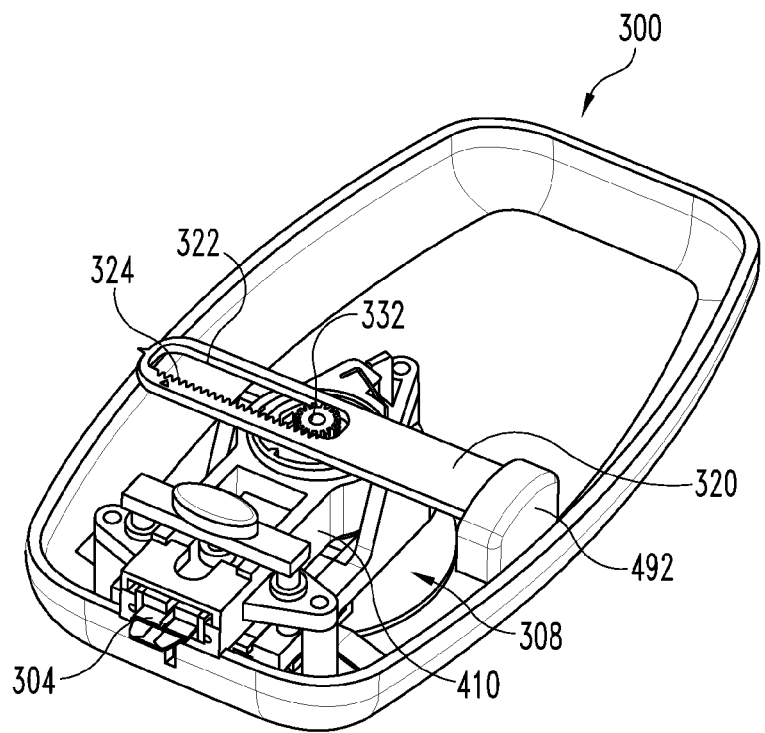
FIG. 15 is a top perspective view of the meter in FIG. 13 with a top cover removed.

As shown in FIG. 15, meter 300 includes a track 320 that spans the width of the meter 300. Side button 492 connects with one end of track 320. Track 320 defines an opening 322 with a plurality of serrations or gear teeth 324 that span a portion of the opening 322. The opening 322 and the plurality of serrations or gear teeth 324 are sized to receive a gear 332 of a stroke adjustable drive system 328 illustrated in FIG. 16. Stroke adjustable drive system 328 includes a wheel 330 that includes a gear 332 having a plurality of serrations or gear teeth 334 that connect with the plurality of serrations 324 on the opening 322. Wheel 330 also includes a pair of arms 336 that are bent in a semi-circular shape. Each of the arms 336 includes a tab 338.

Figure 16:
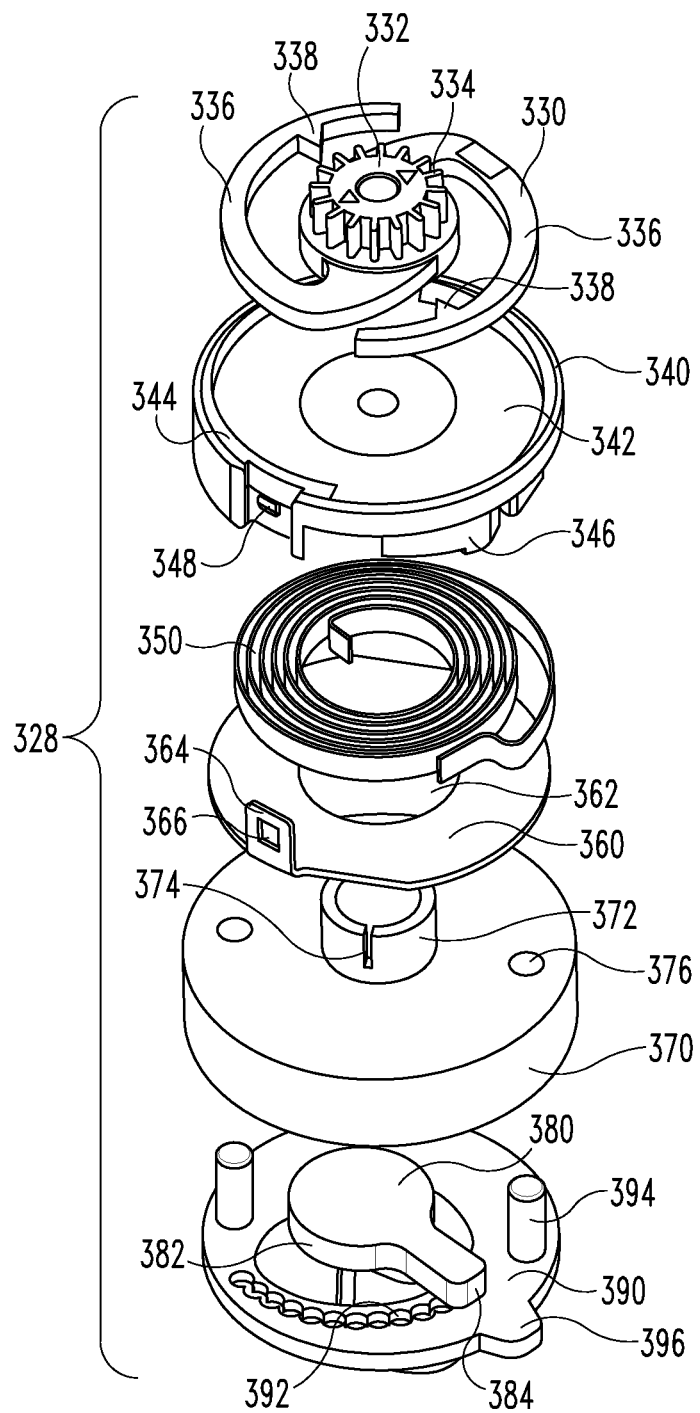
FIG. 16 is an exploded view of a stroke adjustment system of the meter in FIG. 13.

Stroke adjustable drive system 328 includes a cap 340 that receives the wheel 330. One side of cap 340 defines a recess 342 that extends to a rim 344. The pair of arms 336 on wheel 330 are configured to rest in the recess 342 and rest against the rim 344 in an interconnecting fashion such that as the pair of arms 336 are rotated the arms 336 engage the rim 344 to rotate the cap 340. The other side of cap 340 includes a track 346. The track 346 is configured to receive a spring 350, another element of the stroke adjustable drive system 328. Cap 340 has a tab 348 on the rim 344. As illustrated, the cap 340 has a circular shape. As shown in FIG. 16, spring 350 is a flat spiral spring.

Stroke adjustable drive system 328 also includes a plate 360 that is sized to receive spring 350. Plate 360 defines an opening 362. Plate 360 has a tongue 364 with an opening 366 sized to receive tab 348 on the cap 340.

Stroke adjustable drive system 328 further includes a receptacle 370 having a projection 372. Projection 372 is circular in shape with a slit 374 that is sized to receive a portion of spring 350. Projection 372 is sized to extend through opening 362 of plate 360. Receptacle 370 further defines a pair of holes 376, each of the holes 376 sized to receive a projection 394 from a drive wheel 390.

Figure 17:
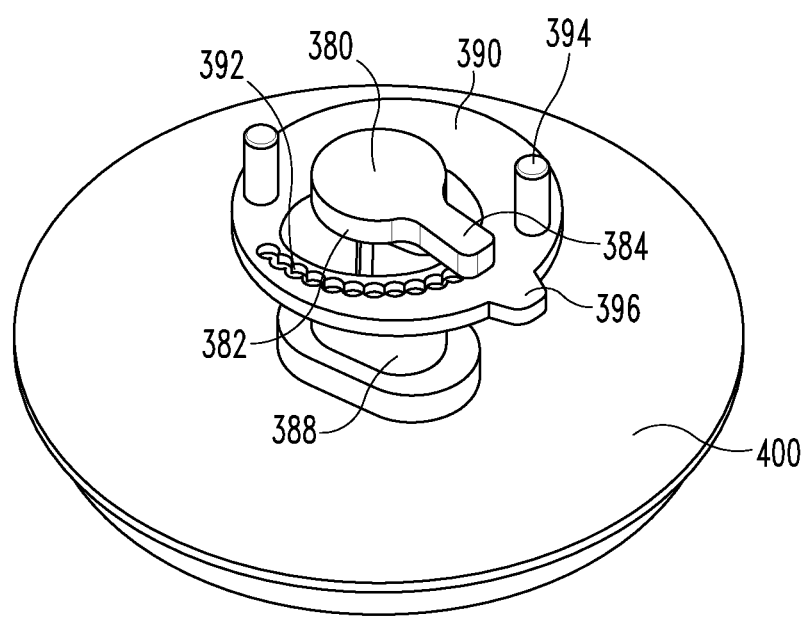
FIG. 17 is top perspective view of a cam and a drive wheel from the stroke adjustment system of FIG. 16.
Figure 18:
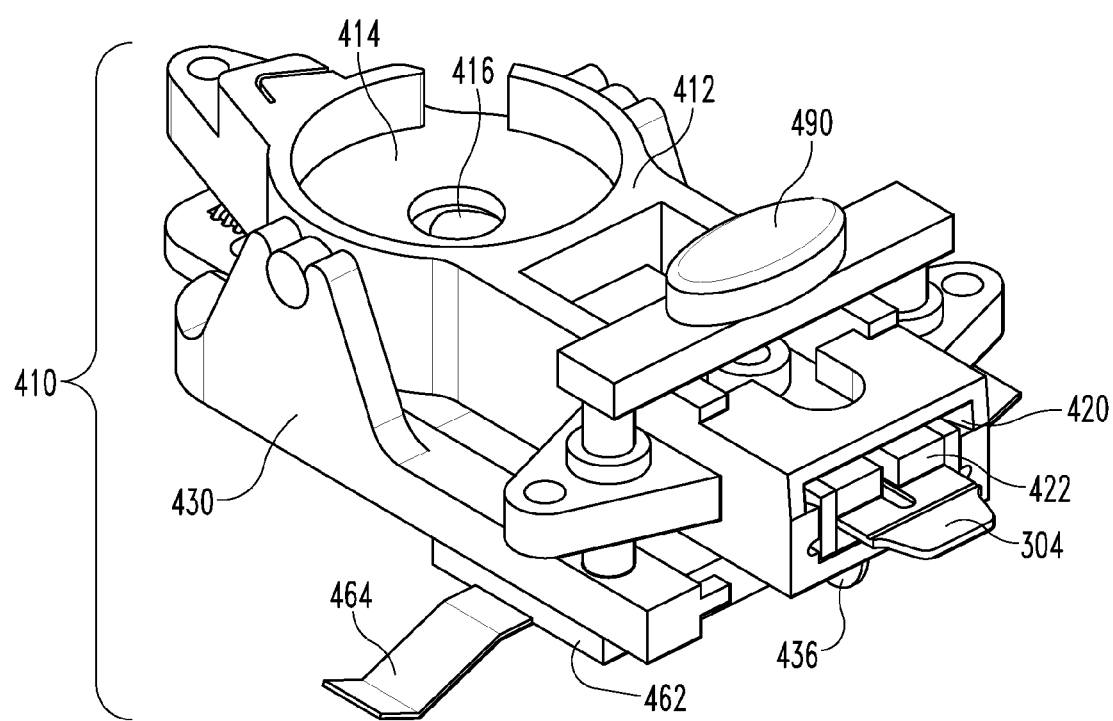
FIG. 18 is a top perspective view of a driver system of the meter in FIG. 13 that receives the stroke adjustment system of FIG. 16.
Figure 19:
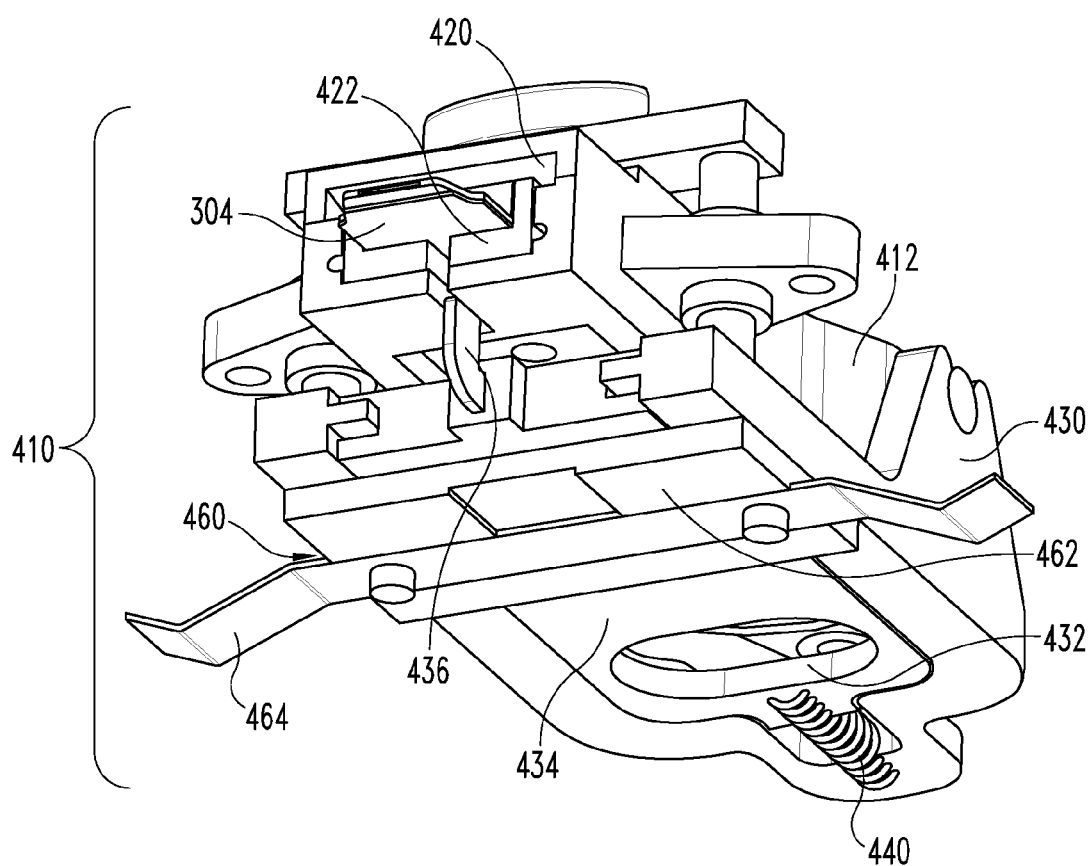
FIG. 19 is a bottom perspective view of the driver system in FIG. 18.
Figure 20:
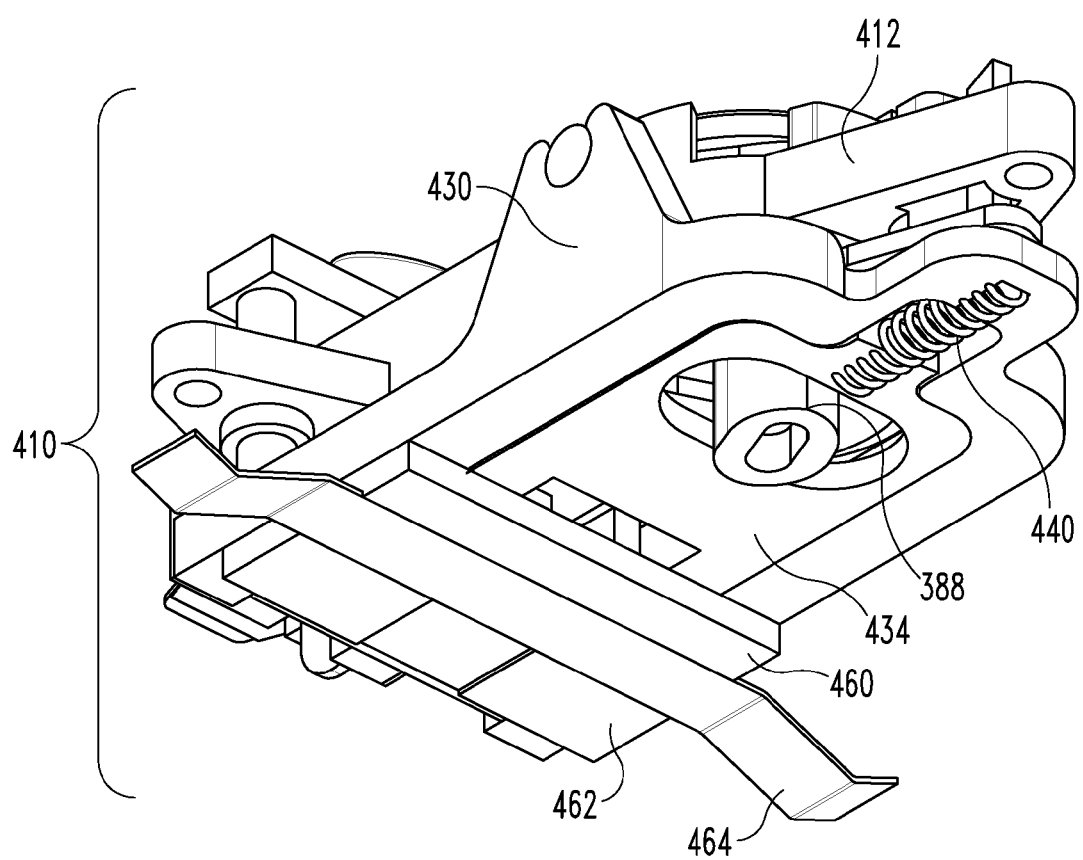
FIG. 20 is a bottom perspective view of the driver system in FIG. 18.

The stroke adjustable drive system 328 also has a cam 380 and a drive wheel 390 that are configured to work together as shown in FIG. 17. Cam 380 includes a body 382 and an arm 384. Arm 384 further includes a peg (not illustrated) sized to fit into one of a plurality of holes 392 on the drive wheel 390. FIG. 17 illustrates the cam 380 and the drive wheel 390 in an initial position in which the drive wheel 390 has no eccentricity. Cam 380 includes a shaft 388 that extends from the body 382 and the arm 384. Shaft 388 extends through an end plate 400 to engage with knob 306. Knob 306 is rotated which in turn rotates cam 380 about drive wheel 390 to adjust the eccentricity of the drive wheel 390 as the peg engages a subsequent one of the plurality of holes 392.

Drive wheel 390 defines a plurality of holes 392 that are each sized to receive peg. Drive wheel 390 also includes a pair of projections 394 that are each sized to extend through one of the pair of holes 376 in receptacle 370. Drive wheel 390 further includes a nub 396.

Figure 21:
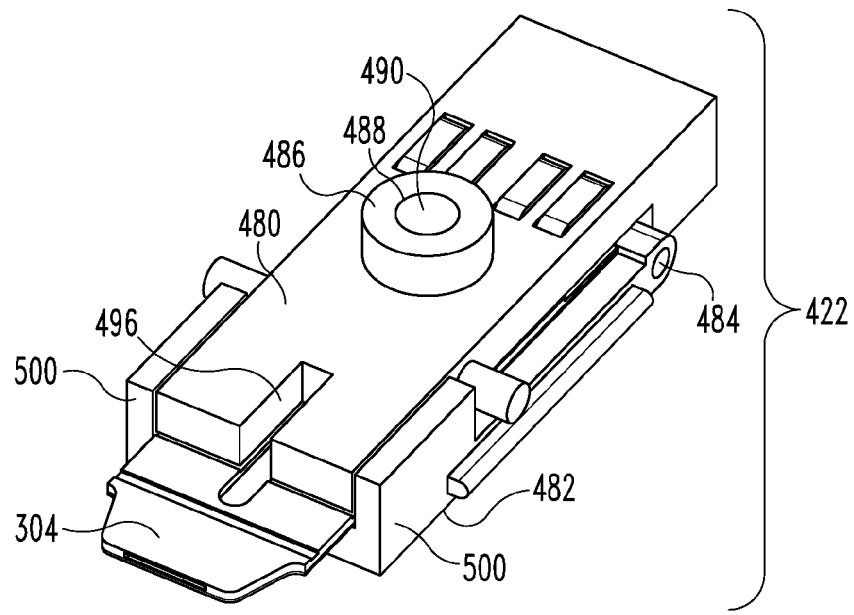
FIG. 21 is a top perspective view of an integrated lancet test strip holder of the meter in FIG. 13.
Figure 22:
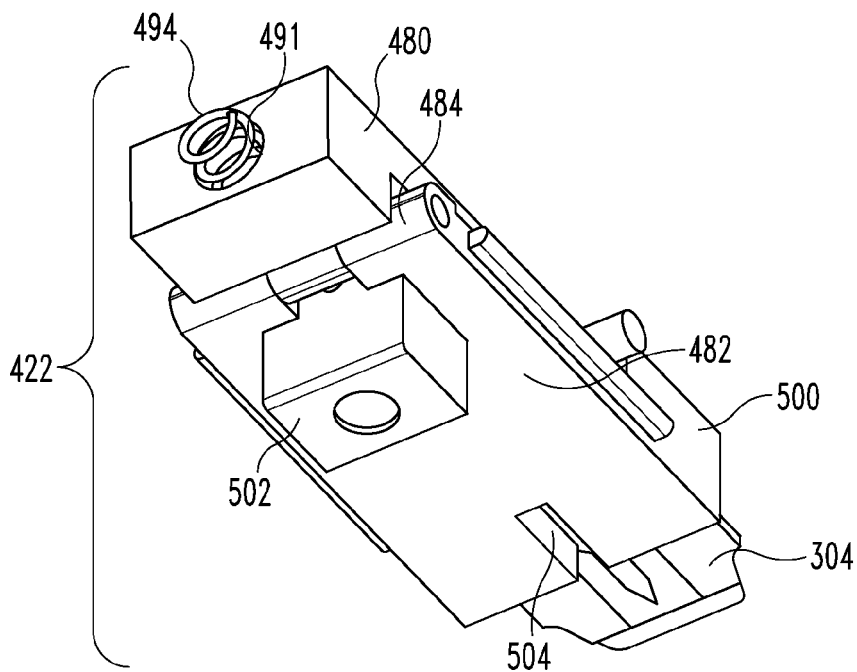
FIG. 22 is a bottom perspective view of the integrated lancet test strip holder in FIG. 21.
Figure 23:
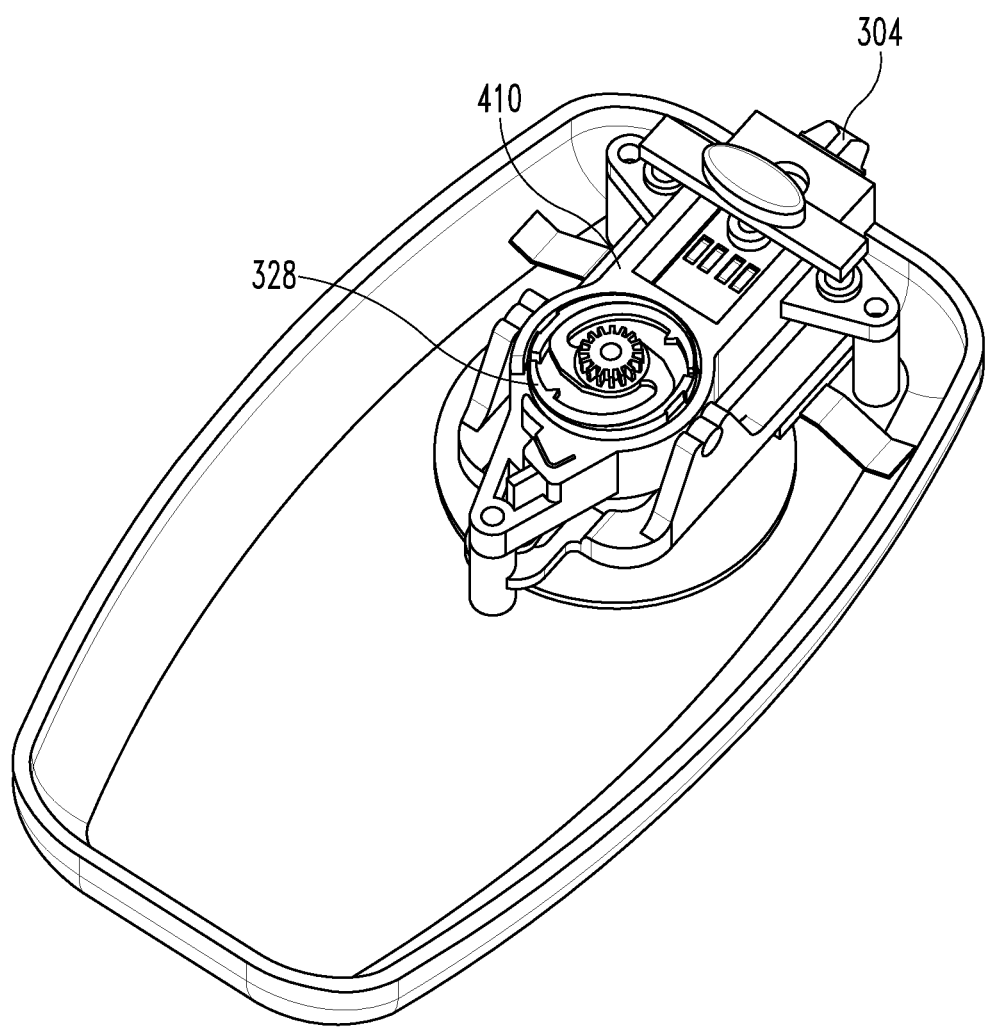
FIG. 23 is a top perspective view of the meter in FIG. 15 with a side button and track removed.

The stroke adjustable drive system 328 is mounted in a driver system 410. Driver system 410 is illustrated in FIGS. 15, 18, 19, 20, 23, and 24. Driver system 410 includes a top platform 412 that defines a compartment 414 sized to receive the wheel 330 and the cap 340. Compartment 414 further defines a hole 416 sized to receive projection 372 of receptacle 370. Top platform 412 further defines a chamber 420 that is configured to hold an integrated lancet test strip holder 422 that receives and holds the integrated lancet test strip 304 is illustrated in FIGS. 21 and 22.

Driver system 410 also includes a bottom platform 430 that receives and holds the top platform 412. Bottom platform 430 also includes a driver 434 and a spring 440 for propelling the driver 434.

Driver 434 defines an opening 432 sized to receive the shaft 388 of the cam 380. Driver 434 includes an arm 436 with a blade (not illustrated) that extends through an engagement notch on the lancet of the integrated lancet test strip 304. At an end opposite to the arm 436, driver 434 has a driving mechanism 440. In the illustrated embodiment, driving mechanism 440 is a spring.

Driver system 410 also includes a mounting platform 460 for attaching the driver system 410 to the bottom side of meter 300. Mounting platform 460 includes a plate 462 and a beam 464. Both the driver 434 and bottom platform 430 rest on the plate 462. However, bottom platform 430 is attached to plate 462 whereas driver 434 slides along plate 462 when the driver 434 is actuated. Beam 464 spans the width of meter 300 and rests on bottom side of meter 300.

As mentioned above, the integrated lancet test strip holder 422 receives and holds the integrated lancet test strip 304 is illustrated in FIGS. 21 and 22. Integrated lancet test strip holder 422 includes a top plate 480 and a bottom plate 482 connected together via a hinge 484. Top plate 480 has a projection 486 that defines a pin hole 488 sized to receive a portion of button 490. Top plate 480 further defines an opening 491 on a rear portion of the top plate 480. A spring 494 is positioned in the opening 491. Spring 494 is compressed to a compact position when the integrated lancet test strip holder 422 is inserted into top platform 412. Top plate 480 further defines a lancet engaging opening 496 that is sized to receive the blade on the driver 434. Bottom plate 482 includes a pair of arms 500 spaced apart from each other a distance that corresponds to the width of the top plate 480. The bottom side of bottom plate 482 has a mounting block 502 that is configured to attach the bottom plate 482 to the top platform 412 when the integrated lancet test strip holder 422 is inserted in the chamber 420. Bottom plate 482 further defines a lancet engaging opening 504 that is sized to receive the blade on the driver 434.

To use meter 300, the integrated lancet test strip holder 422 holding the integrated lancet test strip 304 is inserted in the chamber 420. The integrated lancet test strip holder 422 is inserted until the spring 494 is depressed to give the user a tactile sensation that the integrated lancet test strip holder 422 is fully inserted. At full insertion, a portion of button 490 is inserted in pin hole 488 of the integrated lancet test strip holder 422. The user can select the depth of penetration of the lancet and the stroke length of the drive system 308 by rotating knob 306 to a desired designator 310. Knob 306 engages with shaft 388 on cam 380 such that rotation of knob 306 also rotates cam 380 about drive wheel 390 to adjust the eccentricity of the drive wheel 390 as the peg on cam 380 engages one of the plurality of holes 392 on drive wheel 390. Correspondingly, as cam 380 is rotated the remaining elements of the stroke adjustable drive system 328 are also rotated which causes gear 332 to rotate and lock the plurality of serrations 334 with the plurality of serrations 324 on the track 320.

After the depth of penetration of the lancet and stroke length of the drive system 308 is selected, side button 492 is depressed to cause a lancing, sampling, and testing event. Beneficially, drive system 308 moves the lancet in a simple harmonic motion upon actuation. Moreover, a low amount of transfer vibration to the user results in a lower amount of pain as compared to other types of drivers. The blade on the driver 434 will extend through the engagement notch on the lancet to engage and drive the lancet to extend from the integrated lancet test strip 304 to form an incision.

Another embodiment of a meter is illustrated in FIGS. 24, 25, 26, and 27. Meter is similar to meter 300 therefore details of meter that are similar to meter 300 will not be described for the sake of brevity. Meter includes a gear 602 for adjusting the stroke length of a drive system 610. Similar to meter 300, a knob 306 is configured to engage the gear 602 such that as a user rotates knob 306, the gear 602 correspondingly rotates to adjust the starting position of a cam 628 as described below. The rotational movement of gear 602 results in a lateral or translational movement of cam 628.

Meter includes a drive system 610. Drive system 610 includes a top platform 612 mounted to a bottom platform 614. The top platform 612 defines an opening 616 that is sized to receive a driver or yoke 618 slidingly mounted therein. Yoke 618 defines a compartment 620 sized to receive a bracket 622. In the illustrated embodiment, bracket 622 has an "I" shape. The bracket 622 is slidably mounted in the compartment 620. In one embodiment, the bracket 622 is slidably mounted on one or more rails positioned in the compartment 620. The location of bracket 622 positioned in compartment 620 forms a first opening 624 and a second opening 626 within compartment 620. First opening 624 is sized to receive a cam 628. A pair of springs 630 connect the bracket 622 to the yoke 618. As such the pair of springs 630 are located in the second opening 626. A blade 632 is mounted to the driver or yoke 618 for engagement with the lancet of an integrated lancet test strip (not illustrated).

Drive system 610 also includes a beam 664 that is connected to the top platform 612. Beam 664 spans the width of meter and rests against the top side of meter 600.

The drive system 610 also includes a split or drive wheel 640. The drive wheel 640 includes a first wheel half 642 and a second wheel half 644. As illustrated, the first wheel half 642 and the second wheel half 644 are each substantially circular in shape. The first wheel half 642 defines a pair of pin openings 650 (one of the pin openings 650 not illustrated) and a slot 652. The second wheel half 644 includes a pair of pins 654, each of the pair of pins 654 sized and positioned to assemble with each of the pin openings 650 to connect the first wheel half 642 with the second wheel half 644. The second wheel half 644 also defines a slot 656 that includes a plurality of serrations or teeth 658. The second wheel half 644 also includes a lobe 660 positioned on the perimeter of the second wheel half 644.

The cam 628 is operatively connected to the gear 602 to adjust the position of the cam 628 and ultimately the range of motion that the yoke 618 will travel during a lancing event. To engage the cam 628 with the drive wheel 640, the cam 628 is mounted to a plate 662 wherein the plate 662 includes a pair of detents 668 that are sized to engage the plurality of serrations or teeth 658 on the slot 656 of the second wheel half 644 when the cam 628 and the plate 662 are assembled with the drive wheel 640. The plate 662 further defines a pair of slits 666 that enable deformation of the plate 662 when the plate 662 is adjusted within the slot 656 as the pair of detents 668 slide over the plurality of serrations or teeth 658. As the gear 602 is rotated by the knob 306, the plate 662 slides within the slot 656 and detents 668 slide over the plurality of teeth 658 to adjust the starting position of the cam 628.

The cam 628 is also operatively connected to portions of the stroke adjustable drive system 328 described previously. In particular, the cam 628 is operatively connected to the gear 332, wheel 330, cap, 340, spring 350, plate 360, and receptacle 370 of the stroke adjustable drive system 328. As such, these portions of the stroke adjustable drive system 328 rotate the cam 628 and correspondingly the drive wheel 640 during a lancing event.

The location of the cam 628 within the slot 656 ultimately determines the depth of penetration of the lancet during a lancing event. If the cam 628 is positioned close to the centerline of the drive wheel 640, then the yoke 618 and corresponding blade 632 will move a smaller distance as compared to the cam 628 positioned further away from the centerline of the drive wheel 640. When the cam 628 is positioned very close to the centerline of the drive wheel 640 then no eccentricity or a small amount of eccentricity results. As such, the lancet will form a shallower or smaller depth of penetration as the yoke 618 will not travel as far as compared to a large eccentricity. Oppositely if the cam 628 is positioned further away from the centerline of the drive wheel 640, then a greater eccentricity results. A greater eccentricity enables the yoke 618 and corresponding blade 632 to move a greater a distance. As such, the lancet will form a deeper penetration depth.

Typically, the lancet within the integrated lancet test strip cannot move backwards or rearwardly of its starting position within the integrated lancet test strip. Moreover, the location of the starting position of the blade 632 must be accurately aligned with the engagement notch in the lancet to move the lancet. Beneficially, the sideways or lateral adjustment of cam 628 does not affect or change the starting position of the blade 632 and yoke 618. As such, as the cam 628 is moved laterally or sideways within the slot 656, the blade 632 and the yoke 618 do not move. Therefore, the blade 632 is aligned and correctly positioned with the engagement notch in the lancet for each lancing event. Advantageously, the lateral adjustment of cam 628 allows an eccentricity to be used which adjusts the range of forward motion of the blade 632 and yoke 618. Moreover, this adjustment determines the limits of the forward travel distance of the blade 632 and yoke 618.

Another benefit of meter is the elimination of deadband. Deadband corresponds to a portion of rotation of a drive wheel where there is no associated movement of the driver. Deadband can cause the driver to vibrate which can result in greater lancet impact when forming an incision. Typically, greater lancet impact results in more pain for the user. The present embodiment eliminates deadband with the configuration of yoke 618, bracket 622, and first opening 624 wherein the cam 628 maintains contact with yoke 618 and continues to press against the yoke 618 upon actuation of a trigger 670 as described next.

The drive system 610 further includes a trigger 670 pivotally mounted to the top platform 612. In the illustrated embodiment, trigger 670 has an "A" shape; however, in other embodiments trigger 670 can be shaped differently. Trigger 670 includes a pair of legs 672 configured to engage and retain lobe 660 of the second wheel half 644 until the trigger 670 is rotated. When the trigger 670 is rotated, the legs 672 rotate past the lobe 660 to enable rotation of the drive wheel 640 as described below.

Figure 24:
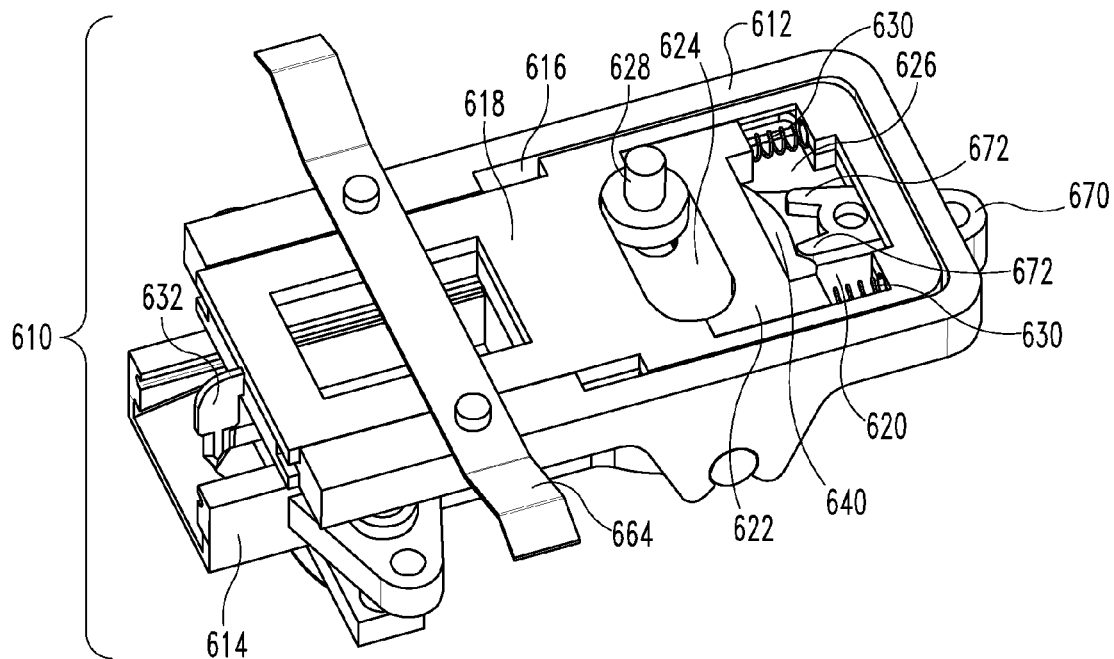
FIG. 24 is a bottom perspective view of a meter with a top cover removed according to a second embodiment.
Figure 25:
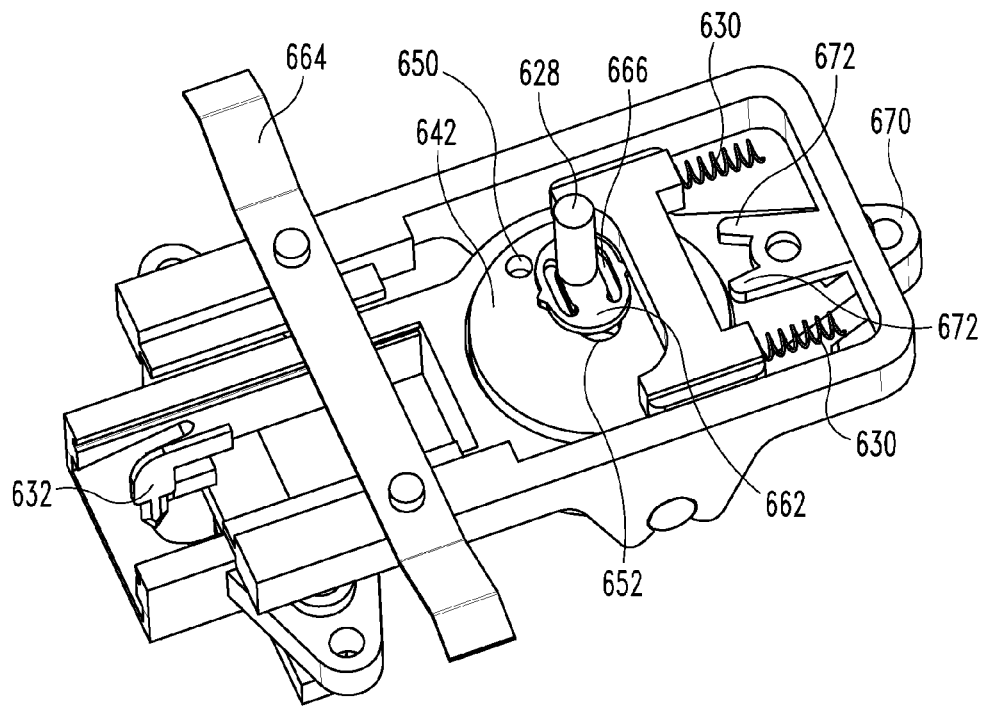
FIG. 25 is a bottom perspective view of the meter in FIG. 24 with a yoke and a driver removed.
Figure 26:
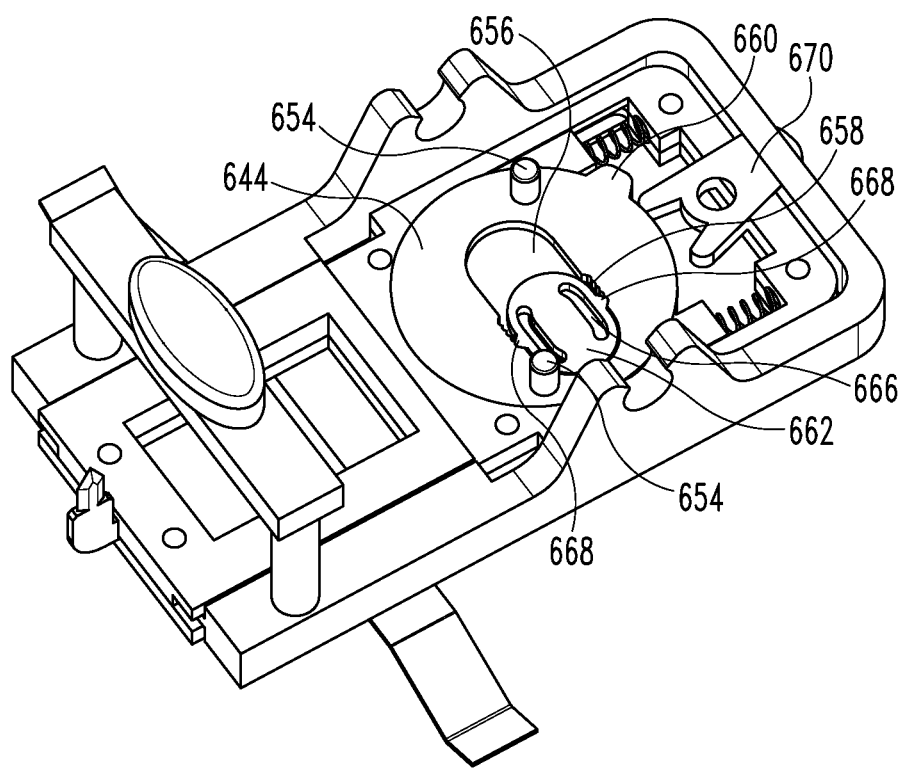
FIG. 26 is a top perspective view of the meter in FIG. 24.
Figure 27:
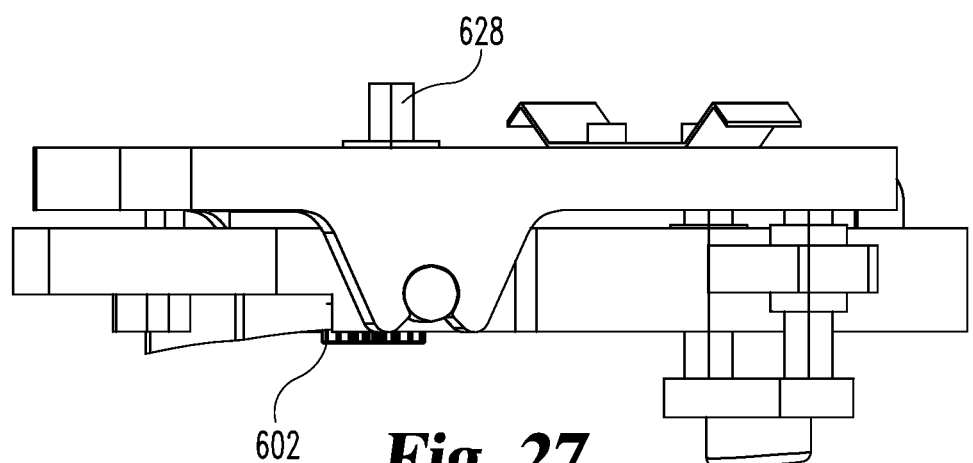
FIG. 27 is a side view of the meter in FIG. 24.

Rotation of cam 628 will be analogized to the counterclockwise movement of a hand on a clock wherein the cam 628 is located in the twelve o'clock or start position as illustrated in FIG. 24. The yoke 618 and blade 632 are in a starting position or a fully retracted position. To adjust the stroke length of the yoke 618 or the distance the yoke 618 travels, the cam 628 is moved laterally in first opening 624 to a desired location by rotation of gear 602 and knob 306. Next, the trigger 670 is rotated or flipped to allow legs 672 adjacent the lobe 660 to slip past lobe 660 of the second wheel half 644 to thereby release the drive wheel 640 for rotation. Next, the spring 350 of the stroke adjustable drive system 328 is released. The spring 350 drives the cam 628 and drive wheel 640 to rotate to the nine o'clock position causing the yoke 618 and blade 632 to move to a fully forward position. During the rotation of cam 628 from twelve to nine o'clock, the bracket 622 also moves with the yoke 618 and blade 632. In the fully forward position, the lancet will form an incision when the meter is placed against the skin of a user. The spring 350 continues to drive the cam 628 and drive wheel 640 to rotate to the six o'clock position. As the cam 628 and drive wheel 640 rotate to the six o'clock position, the yoke 618 and blade 632 are retracted to the starting position thereby retracting the lancet rearwardly within the test strip. During the rotation of cam 628 from nine to six o'clock, the bracket 622 moves with the yoke 618 and blade 632 to its starting position. The spring 350 continues to drive the cam 628 and the drive wheel 640 to rotate to the three o'clock position wherein the cam 628 pushes against the bracket 622 to slide the bracket 622 toward the rear of the yoke 618 while the yoke 618 remains in its starting position. As the bracket 622 slides to rear of the yoke 618, the springs 630 compress. When the bracket 622 is moved near or against the rear of the yoke 618, the cam 628 and the drive wheel 640 rotate from the three o'clock position to the twelve o'clock position as the compressed springs 630 return to a relaxed state. In the twelve o'clock position, the lobe 660 again contacts one of the legs 672 wherein this interaction restrains the drive wheel 640 from further rotation. By changing the stroke length of the driver or yoke 618, the penetration depth of the lancet of the integrated lancet test strip is adjusted or changed during the priming of the driver or yoke 618.

Figure 28:
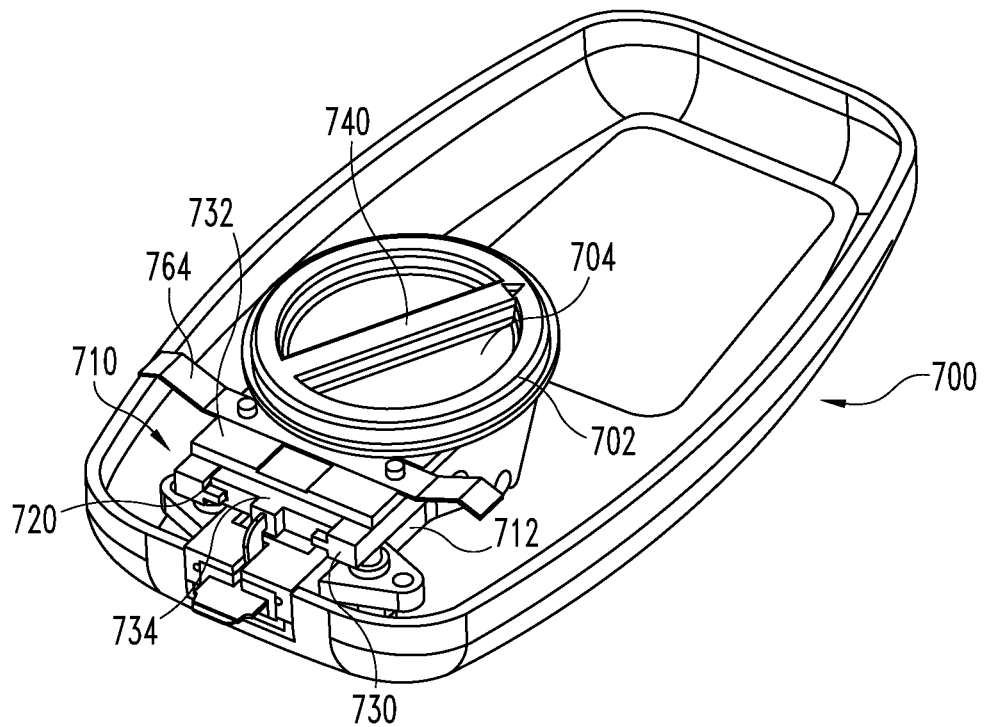
FIG. 28 is a bottom perspective view of a meter with a top cover removed according to a third embodiment.

Another type of a meter 700 that is similar to meter 300 is illustrated in FIG. 28. Details of meter 700 that are similar to meter 300 will not be described for the sake of brevity. Meter 700 includes an outer wheel 702 and an inner wheel 704 for adjusting the stroke length of a drive system 710. The stroke length of the drive system 710 is a function of the eccentricity of the inner wheel 704. With meter 700, the stroke length of the drive system 710 is adjusted by pressing and turning the outer wheel 702 to engage the inner wheel 704 and adjust the eccentricity of the inner wheel 704 as described in more detail below.

Meter 700 includes a drive system 710. Drive system 710 includes a top platform 712 and a bottom platform 730 wherein the top platform 712 is mounted to the bottom platform 730. Bottom platform 730 also defines a driver opening 720 that is sized to receive a driver 734 slidingly mounted therein. Meter 700 includes a plate 732 onto which the bottom platform 730 is mounted. Meter 700 also includes a beam 764 that is attached to the plate 732 and spans from the plate 732 to an edge of the meter 700.

Outer wheel 702 includes a bar 740 that spans across the width of the outer wheel 702. The outer wheel 702 functions like a dial. To adjust the stroke length of the drive system 710, a user presses and rotates the outer wheel 702 to turn it to different detent positions to adjust the eccentricity of the inner wheel 704. The movement of the inner wheel 704 causes the driver 734 to move a desired increment in the driver opening 720. By moving the driver 734 to a desired location in the driver opening 720, the stroke length of the driver 734 is changed. By changing the stroke length of the driver 734, the penetration depth of the lancet of the integrated lancet test strip is adjusted or changed prior to actuation of the driver 734.

In either the fixed stroke lancet drive system or the variable drive stroke lancing system, the test strip of the integrated lancet test strip is held stationary or fixed during the lancing, sampling, and testing events. Illustrated in FIG. 29, the integrated lancet test strip 58 includes two mechanisms that allow the test strip 65 to be immobilized while the lancet 62 is actuated. One embodiment of the integrated lancet test strip 58 defines an opening 900 positioned behind or rear of the lancet 62. Another embodiment of the integrated lancet test strip 58 defines a pair of vee notches 902, wherein each of the vee notches 902 is located along a side of the test strip 65.

Figure 29:
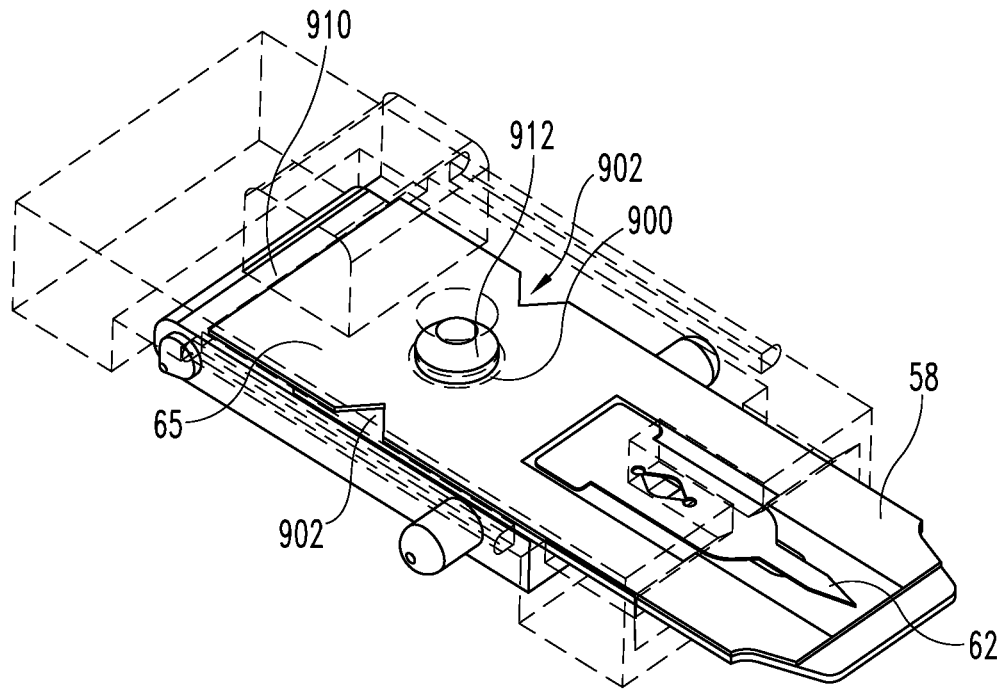
FIG. 29 is a bottom perspective view of a top plate of an integrated lancet test strip holder and an integrated lancet test strip.
Figure 30:
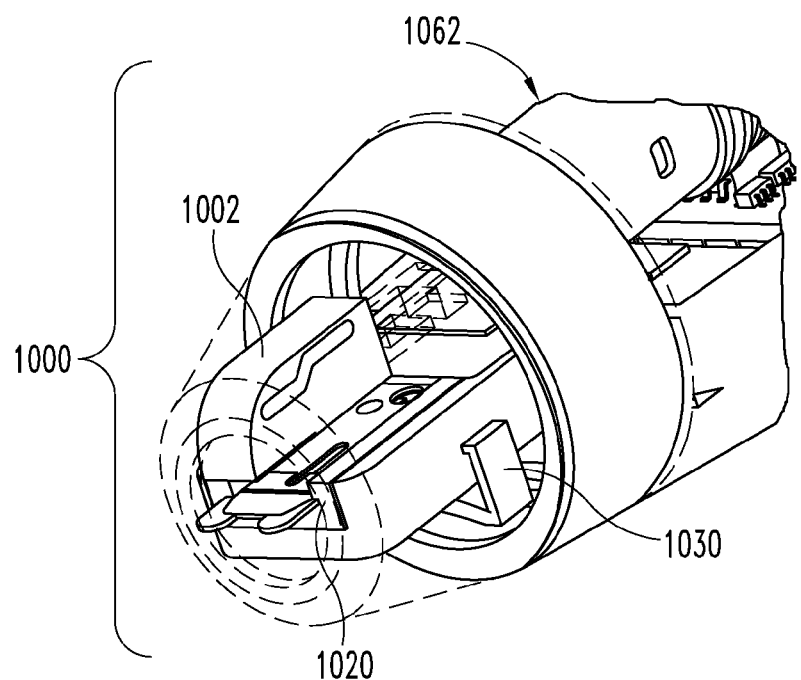
FIG. 30 is a perspective view of a single cam of an engagement system with an integrated lancet test strip.
Figure 31:
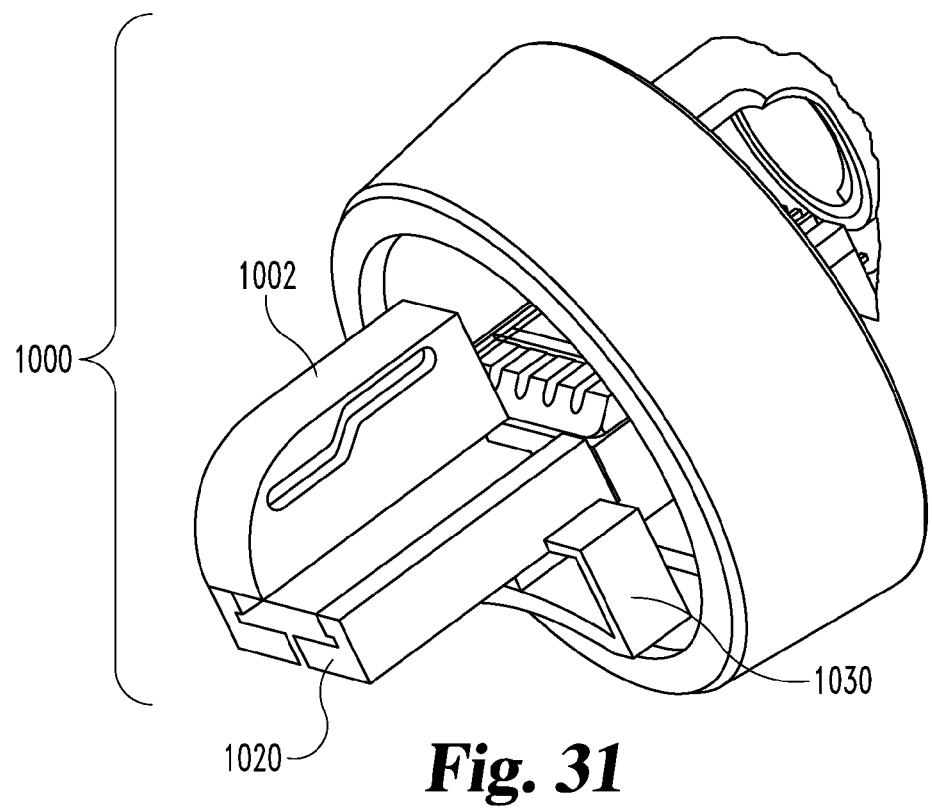
FIG. 31 is a perspective view of the single cam of an engagement system in FIG. 30 without an integrated lancet test strip.
Figure 32:
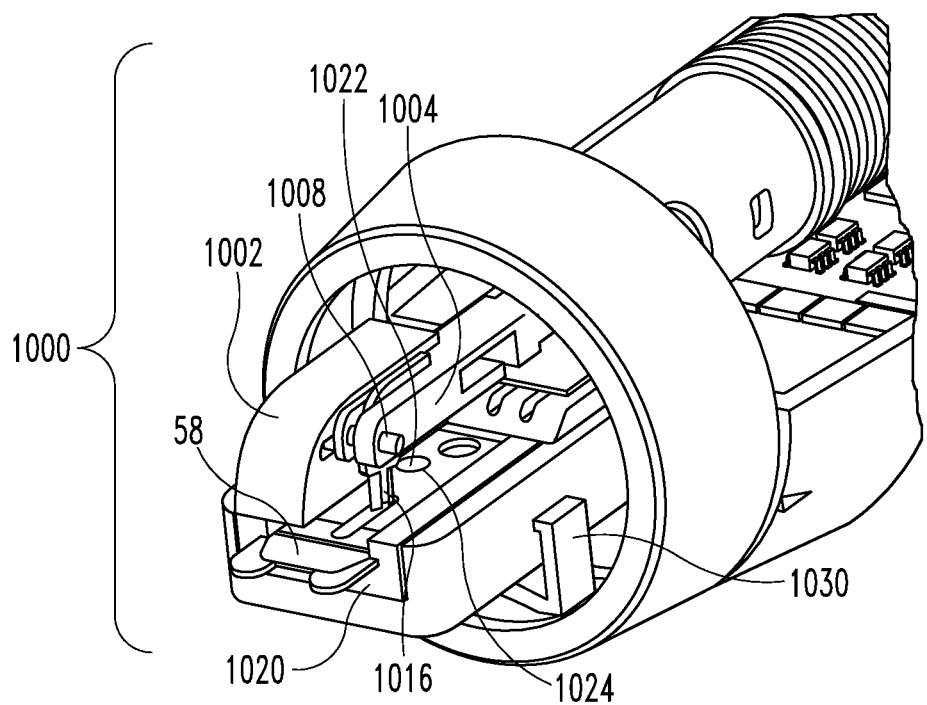
FIG. 32 is a perspective view of the single cam of an engagement system in FIG. 30 with a driver.
Figure 33:
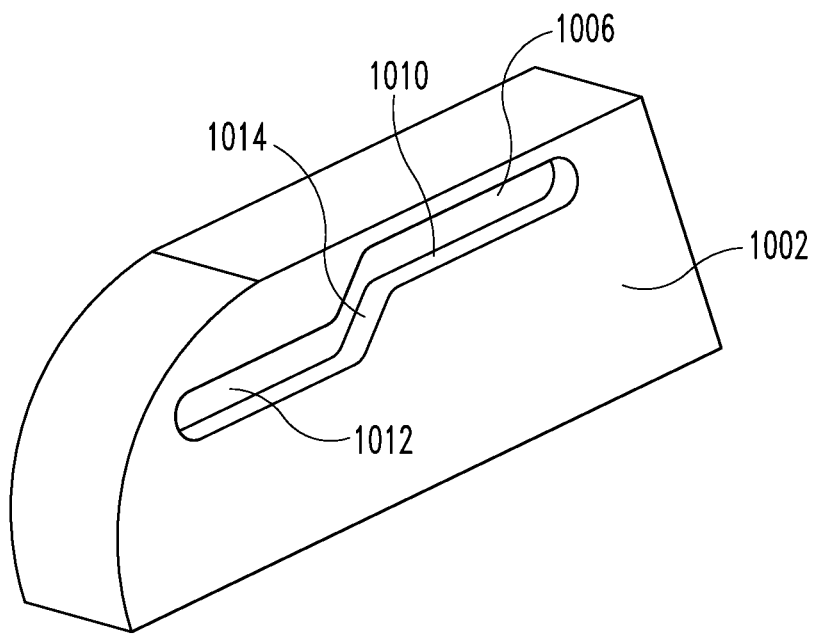
FIG. 33 is a perspective view of the single cam in FIG. 30.

A top plate 910 similar to top plate 480 is also illustrated in FIG. 29; however, for the sake of brevity similar features will not be discussed. Similar to top plate 480, top plate 910 is part of an integrated lancet test strip holder. Top plate 910 has a pin 912 that is sized to enter opening 900 and locate or properly position the integrated lancet test strip 58 in an integrated lancet test strip holder. The pin 912 in opening 900 also retains the test strip 65 when the lancet 62 is actuated. Therefore, the lancet 62 is free to move relative to the test strip 65 while the test strip 65 is immobilized. In another form not illustrated, top plate 910 includes a pair of pins that are sized to retain each of the vee notches 902 and the test strip 65 of the integrated lancet test strip 58. The pins in vee notches 902 also aid in properly positioning the integrated lancet test strip 58 in an integrated lancet test strip holder.

In another embodiment illustrated in FIGS. 30, 31, 32, and 33, an engagement system 1000 is illustrated. Engagement system 1000 includes a cam 1002 and a driver 1004 connected to a drive actuator 1062. The cam 1002 defines a pin slot 1006 that is configured to receive a pin 1008 from the driver 1004. Pin slot 1006 has a top portion 1010 that connects with a bottom portion 1012 via an angled portion 1014. As described in more detail below, the pin 1008 rides or slides in the pin slot 1006 from the top portion 1010 along the angled portion 1014 to the bottom portion 1012 upon actuation of the driver 1004. The driver 1004 includes a pin 1008 and blade 1016 that engages and moves the lancet 62 of the integrated lancet test strip 58.

The engagement system 1000 further includes an integrated lancet test strip holder 1020 that holds the integrated lancet test strip 58. The engagement system 1000 also includes a spring 1030 that has a pin 1022 that is inserted in a hole 1024 in the integrated lancet test strip 58 to retain the test strip while the lancet is actuated. The spring 1030 is moveable to adjust the starting position of the integrated lancet test strip 58 prior to actuation of the driver 1004.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. An apparatus, comprising:
   an integrated lancing test strip including a lancet for forming an incision in tissue and a test strip configured to analyze a body fluid sample;
   a driver system configured to move the lancet to form an incision, the driver system having a fixed stroke length to move the lancet, the driver system including:
      a driver configured to fire the lancet, the driver having an extension mechanism;
      a drive actuator;
      a cam engagement member configured to connect the drive actuator with the driver, the cam engagement member defines a first opening sized to receive the extension mechanism, wherein the drive actuator is configured to move the cam engagement member; and
      an engagement mechanism configures to hold the test strip stationary while the lancet is moved to form the incision in tissue, the engagement mechanism configured to receive the driver and the cam engagement member, the engagement mechanism defines a second opening sized to receive the extension mechanism, wherein the first opening and the second opening are arranged to limit a distance the driver moves when the driver fires the lancet; and
   an adjustment mechanism configured to move the driver system to adjust a starting position of the driver system, to adjust a distance the extension mechanism travels in the first and the second openings, and to adjust the depth of penetration of the lancet in tissue.

2. The apparatus of claim 1, wherein the adjustment mechanism is positioned on the engagement mechanism and the adjustment mechanism is configured to adjust a starting position of the cam engagement member.

3. The apparatus of claim 1, wherein the adjustment mechanism is positioned on the drive actuator and the adjustment mechanism is configured to adjust a starting position of a firing mechanism.

4. The apparatus of claim 1, wherein the adjustment mechanism is positioned on a drive shaft and the adjustment mechanism is configured to adjust a starting position of the cam engagement member.

5. An apparatus, comprising:
   an integrated lancing test strip including a lancet configured to form an incision in tissue and a test strip configured to analyze a body fluid sample;
   an integrated lancet test strip holder to hold the test strip stationary while the lancet forms the incision;
   a driver system configured to move the lancet to form an incision, the driver system having a variable stroke length to move the lancet, the driver system including:
      a driver configured to move the lancet;
      a drive wheel that is rotatable to adjust the stroke length of the driver;
      a cam that is movable to adjust an eccentricity of the drive wheel and a stroke length of the lancet; and
      a platform configured to receive and retain the integrated lancet test strip holder.

6. The apparatus of claim 5, wherein the drive wheel includes a plurality of holes and the cam includes a peg sized to fit into one of the plurality of holes as the cam is rotated about the drive wheel.

7. The apparatus of claim 5, wherein the cam is configured to slide in a lateral direction relative to the direction of lancing to adjust the eccentricity of the drive wheel.

8. The apparatus of claim 7, further comprising a yoke configured to engage and move the lancet, wherein a lateral adjustment of the cam does not change a starting position of the yoke.

9. The apparatus of claim 5, wherein the cam is configured to rotate to adjust an eccentricity of the drive wheel.

10. The apparatus of claim 5, wherein the integrated lancet test strip holder defines an opening sized to receive a portion of the driver that moves the lancet to form the incision.

11. The apparatus of claim 5, wherein the test strip includes a first feature and the integrated lancet test strip holder includes a second feature sized to matingly engage the first feature on the test strip.

12. A method, comprising:
providing an integrated lancing test strip including a lancet for forming an incision in tissue and a test strip configured to analyze a body fluid sample;
providing an integrated lancet test strip holder to hold the test strip stationary while the lancet forms the incision;
providing a driver system configured to receive a driver and the integrated lancing test strip holder, wherein the driver is configured to move the lancet;
modifying a stroke length of the driver by moving a cam prior to actuation of the lancet, wherein the modified stroke length adjusts a penetration depth of the lancet in tissue, wherein the cam moves closer to a centerline of the driver to reduce the penetration depth of the lancet and the cam moves further away from the centerline of the driver to increase the penetration depth of the lancet; and
holding the test strip stationary in the integrated lancet test strip holder.

13. The method of claim 12, wherein the moving the cam includes sliding the cam perpendicular to a direction of lancing.

14. The method of claim 12, further comprising:
a drive wheel defines a plurality of openings; and
the moving the cam includes rotating the cam wherein a peg on the cam engages one of the plurality of openings on the drive wheel.

15. The method of claim 12, further comprising:
the lancet defines an engagement notch sized to receive the driver; and
the modifying the stroke length of the driver includes maintaining alignment of the driver with the engagement notch.

16. The method of claim 12, wherein the modifying the stroke length of the driver maintains a starting position of the driver at a constant position.

* * * * *

UNITED STATES PATENT AND TRADEMARK OFFICE
CERTIFICATE OF CORRECTION

PATENT NO.         : 9,167,992 B2
APPLICATION NO.    : 12/938858
DATED              : October 27, 2015
INVENTOR(S)        : Steven N. Roe It is certified that error appears in the above-identified patent and that said Letters Patent is hereby corrected as shown below:

In the Claims
Col. 14, Claim 1, line 7, replace "configures" with --configured--

Signed and Sealed this
Fourteenth Day of June, 2016

Michelle K. Lee
*Director of the United States Patent and Trademark Office*